(12) United States Patent
Kausek

(10) Patent No.: US 8,679,042 B2
(45) Date of Patent: Mar. 25, 2014

(54) ORTHOTIC BRACE

(76) Inventor: James H. Kausek, Swampscott, MA (US)

( * ) Notice: Subject to any disclaimer, the term of this patent is extended or adjusted under 35 U.S.C. 154(b) by 301 days.

(21) Appl. No.: 12/807,659

(22) Filed: Sep. 10, 2010

(65) Prior Publication Data

US 2011/0004135 A1  Jan. 6, 2011

Related U.S. Application Data

(63) Continuation-in-part of application No. PCT/US2009/001537, filed on Mar. 10, 2009.

(60) Provisional application No. 61/068,763, filed on Mar. 10, 2008, provisional application No. 61/069,870, filed on Mar. 18, 2008.

(51) Int. Cl.
*A61F 5/00* (2006.01)

(52) U.S. Cl.
USPC .................................. 602/16; 602/20; 602/23

(58) Field of Classification Search
USPC .............. 602/5, 13, 16, 20–29; 128/878–879, 128/882; 5/624
See application file for complete search history.

(56) References Cited

U.S. PATENT DOCUMENTS

| | | | |
|---|---|---|---|
| 1,622,211 A | 3/1927 | Sheehan | |
| 3,528,412 A | 9/1970 | McDavid | |
| 3,581,741 A | 6/1971 | Rosman | |
| 4,111,194 A * | 9/1978 | Cox et al. | 602/26 |
| 4,219,892 A * | 9/1980 | Rigdon | 2/24 |
| 4,337,764 A | 7/1982 | Lerman | |
| 4,381,768 A | 5/1983 | Erichsen et al. | |
| 4,400,820 A * | 8/1983 | O'Dell et al. | 378/209 |
| 4,805,606 A | 2/1989 | McDavid, III | |
| 4,938,207 A | 7/1990 | Vargo | |
| 4,940,045 A | 7/1990 | Cromartie | |
| 5,002,045 A | 3/1991 | Spademan | |
| 5,185,000 A * | 2/1993 | Brandt et al. | 602/63 |
| 5,277,698 A | 1/1994 | Taylor | |
| 5,288,287 A | 2/1994 | Castillo et al. | |
| 5,458,565 A | 10/1995 | Tillinghast, III | |
| 5,520,622 A * | 5/1996 | Bastyr et al. | 602/16 |
| 5,542,911 A | 8/1996 | Cassford et al. | |
| 5,669,873 A | 9/1997 | Towsley | |
| 5,823,931 A | 10/1998 | Gilmour | |
| 5,857,989 A | 1/1999 | Smith, III | |

(Continued)

FOREIGN PATENT DOCUMENTS

WO  PCT/US2005/008010  9/2006

OTHER PUBLICATIONS

Innovation Sports Performance Bracing product catalog, (date unknown).

(Continued)

*Primary Examiner* — Michael A. Brown
(74) *Attorney, Agent, or Firm* — Bergman & Song LLP; Michael Bergman

(57) ABSTRACT

A brace for supporting a biomechanical joint includes first and second surface regions disposed relatively distal to the joint on a first side of a limb and a third surface region disposed substantially adjacent to the joint on a second side of the limb so that by applying forces between the surface regions, a portion of the joint is cantilevered and pressure is relieved from a cartilage surface region within the joint.

22 Claims, 35 Drawing Sheets

(56) References Cited

U.S. PATENT DOCUMENTS

| | | |
|---|---|---|
| 6,287,268 B1 | 9/2001 | Gilmour |
| 6,387,066 B1 | 5/2002 | Whiteside |
| 6,527,733 B1 | 3/2003 | Ceriani et al. |
| 6,551,264 B1 | 4/2003 | Cawley et al. |
| 6,875,187 B2 | 4/2005 | Castillo |
| 6,981,957 B2 | 1/2006 | Knecht et al. |
| 6,994,682 B2 * | 2/2006 | Bauerfeind et al. ............ 602/26 |
| 7,044,926 B2 | 5/2006 | Carlson |
| 7,198,610 B2 | 4/2007 | Ingimundarson et al. |
| 7,758,527 B2 * | 7/2010 | Gilmour et al. ................ 602/23 |
| 2004/0068215 A1 | 4/2004 | Adelson et al. |
| 2004/0267179 A1 | 12/2004 | Lerman |
| 2005/0203455 A1 | 9/2005 | Cropper |
| 2007/0185425 A1 | 8/2007 | Einarssom et al. |
| 2007/0197946 A1 | 8/2007 | Gilmour |
| 2007/0213648 A1 | 9/2007 | Ferrigolo et al. |

OTHER PUBLICATIONS

The Unloader Questions and Answers datasheet, Apr. 1994 or earlier.
Ossur Unloader One product brochure, Mar. 2006.
Generation II USA Inc. product catalog, Apr. 1994 or later.
Generation II USA Inc. The New Unloader Express datasheet, Oct. 1996 or later.
Generation II USA Inc. product catalog, 2000 or later.
Generation II Unloader Bi-Com PF datasheet, Oct. 1996 or later.
Bledsoe Thruster 2 OA Knee Brace brochure, Nov. 2004.
Bledsoe Thruster MA datasheet, Jan. 2002.
Bledsoe Aligner LA OA Knee Brace datasheet, Apr. 2004.
Step Free OA data sheet, Oct. 1998 or later.

* cited by examiner

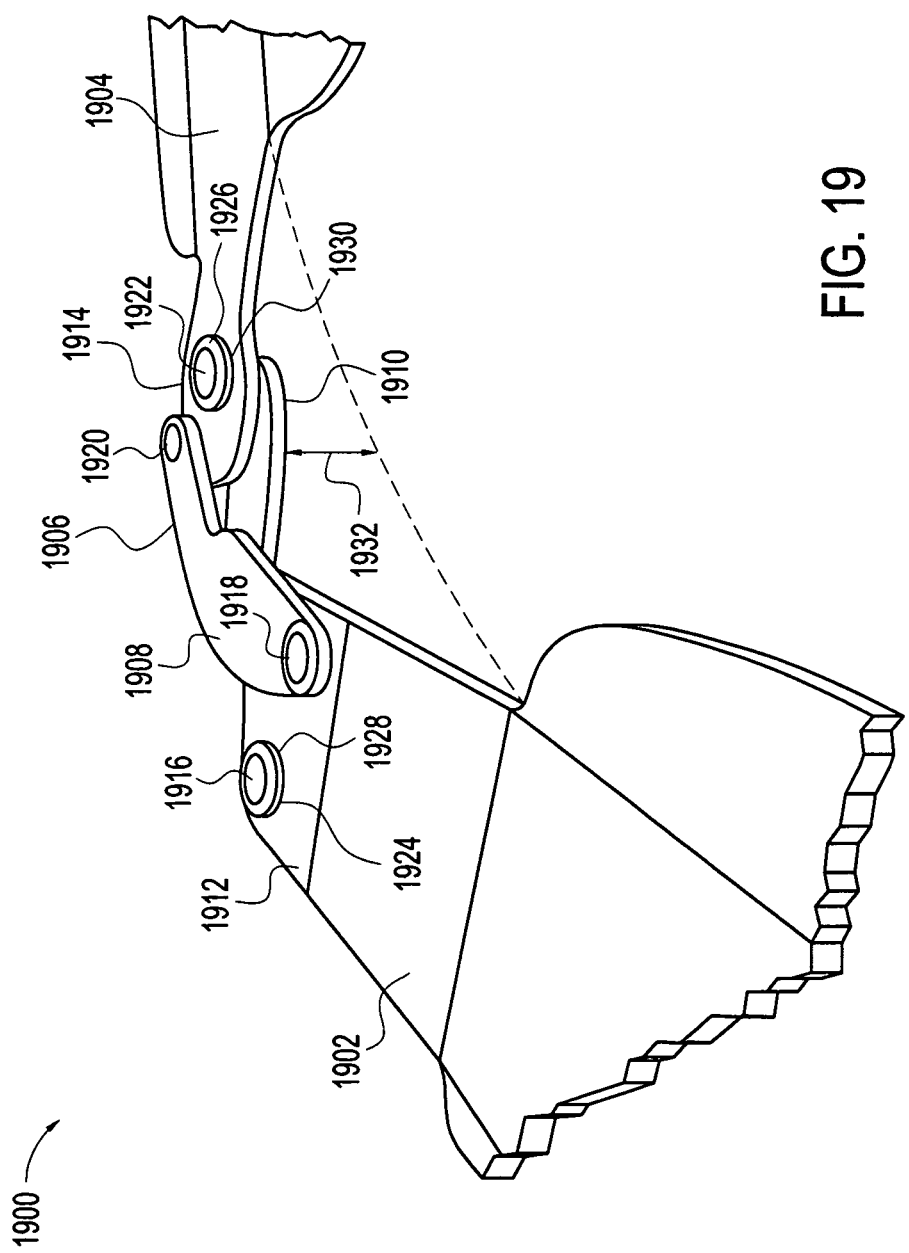

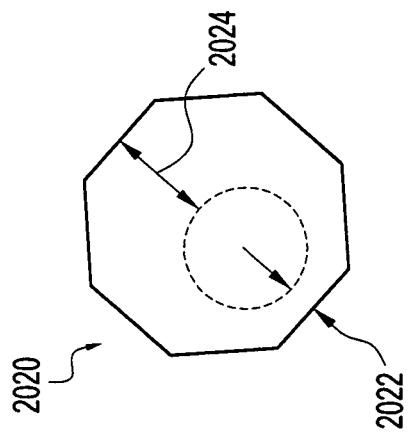
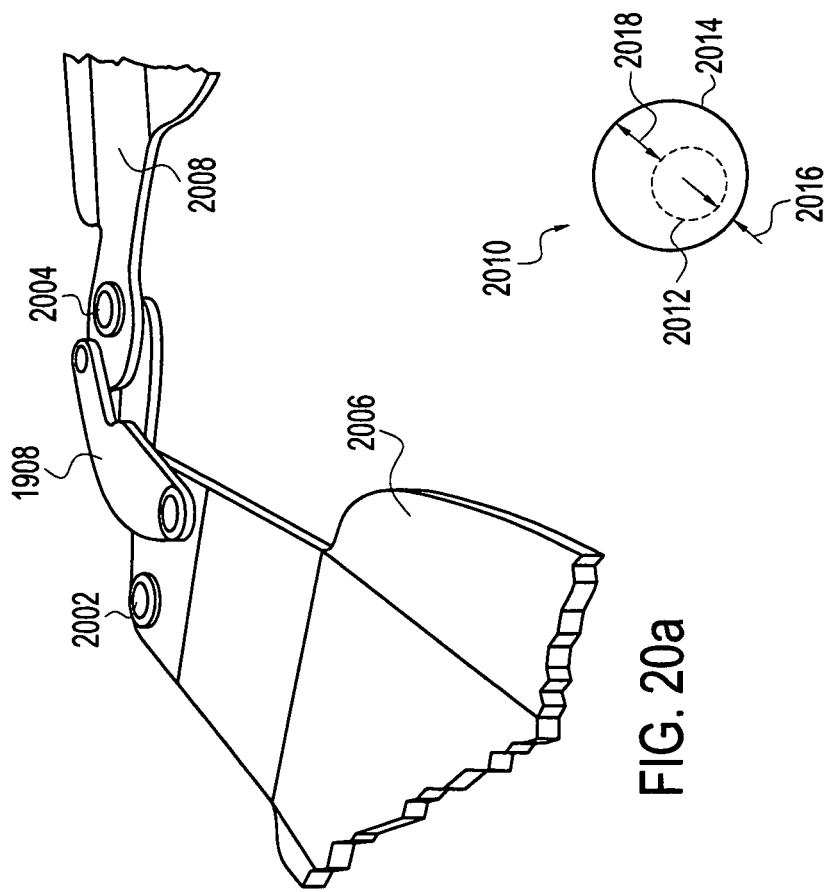

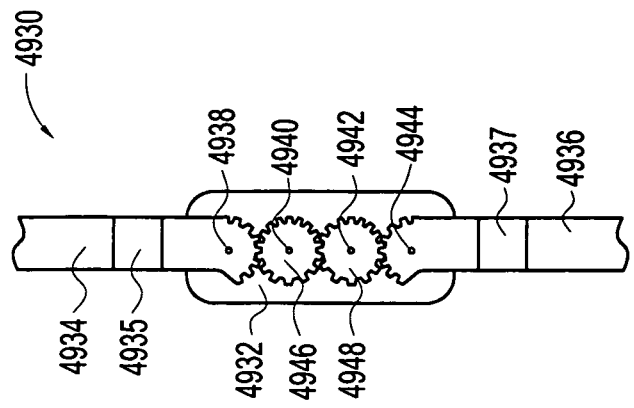
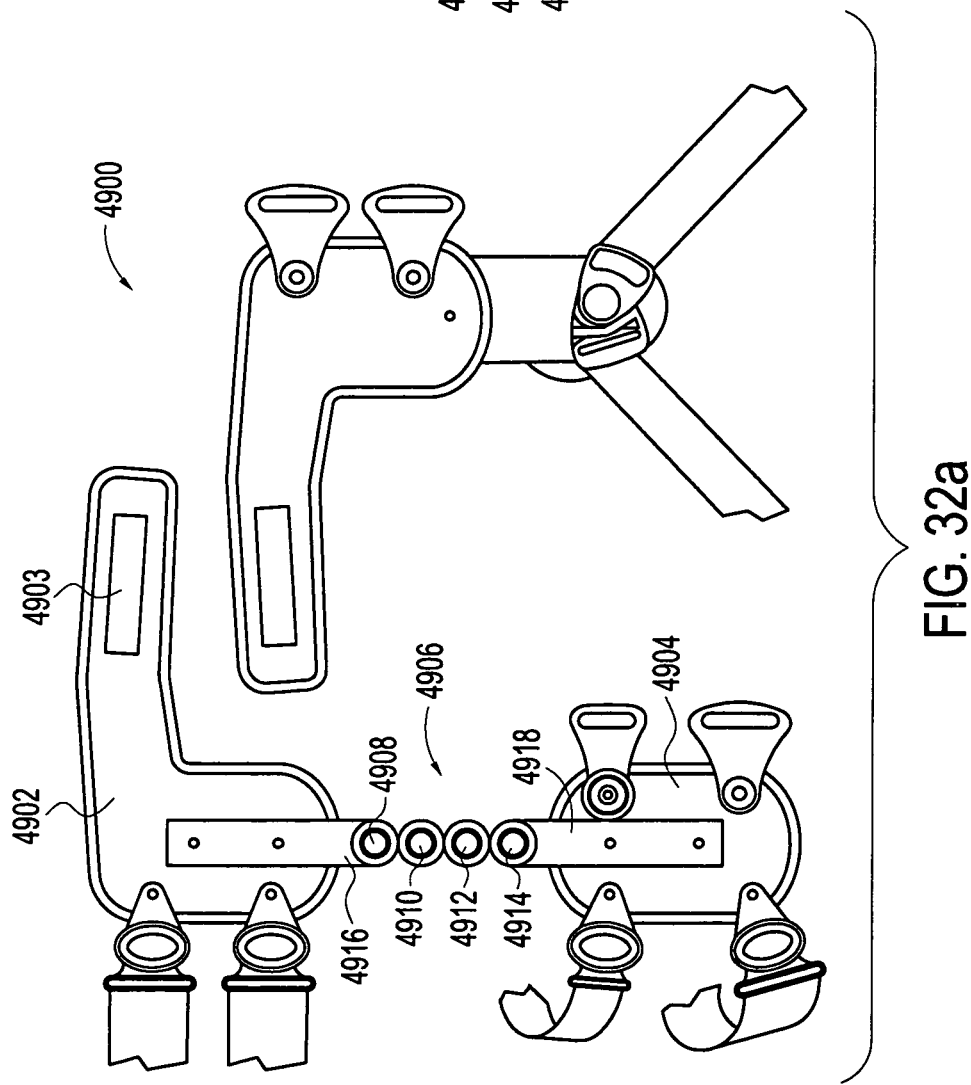

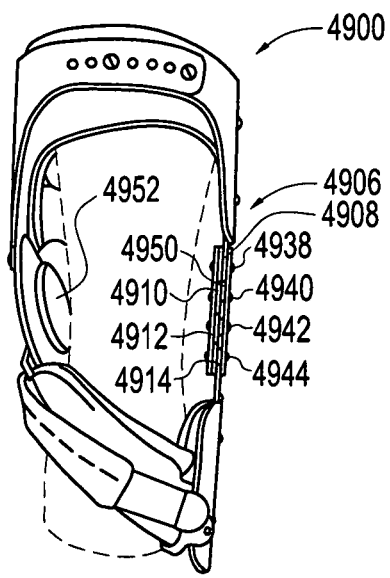
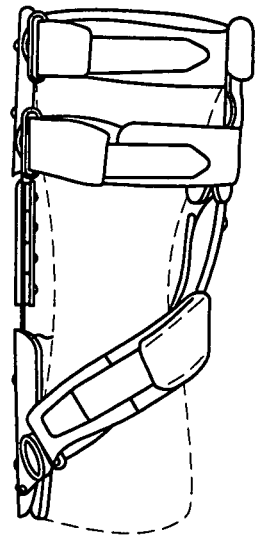
FIG. 33a  FIG. 33b
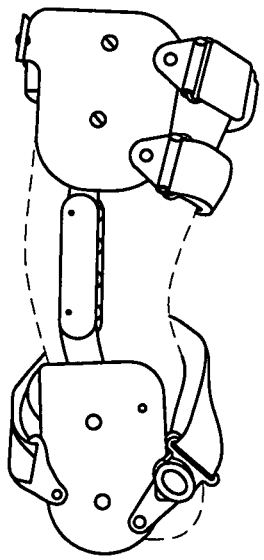
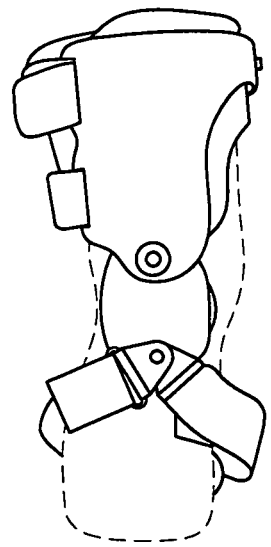
FIG. 33c  FIG. 33d

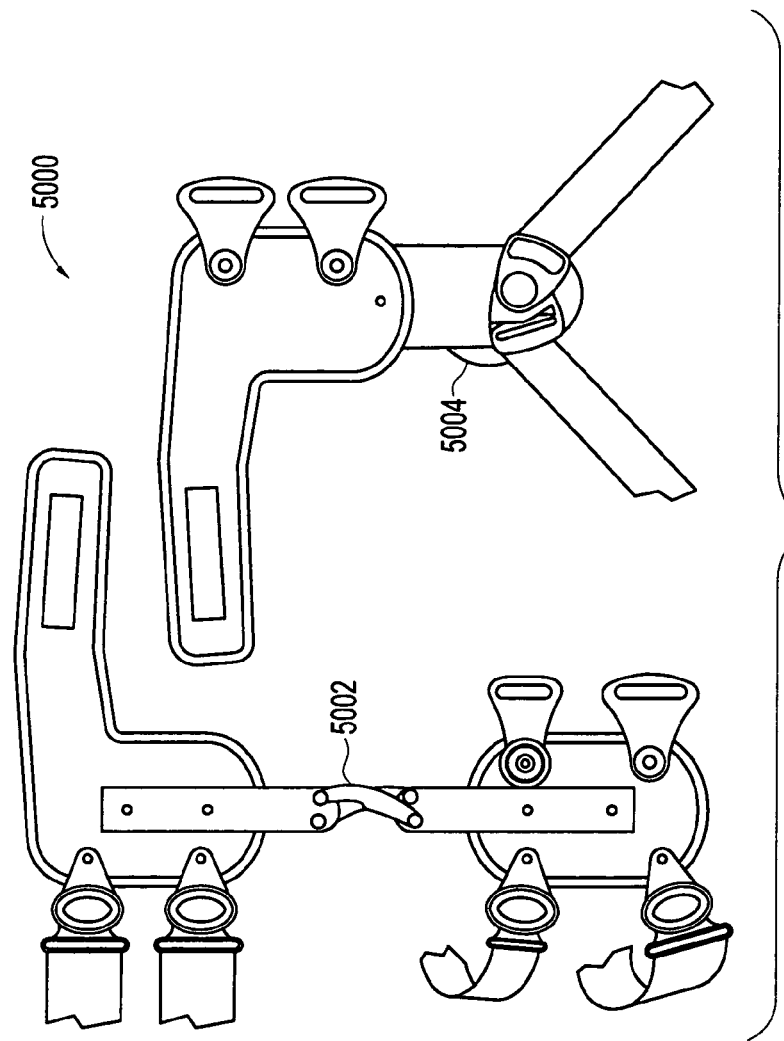
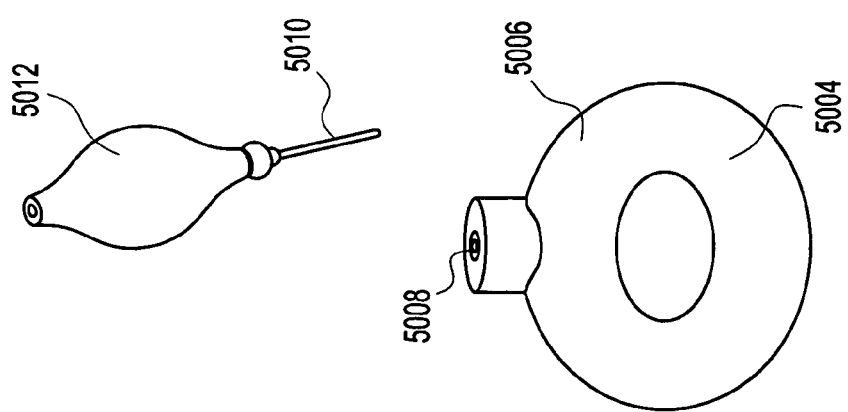
FIG. 34a
FIG. 34b

ORTHOTIC BRACE

The present invention is a Continuation-in-Part of PCT Application number PCT/US 2009/001537 having an international filing date of Mar. 10, 2009, the disclosure of which is herewith incorporated by reference in its entirety, which in turn claims priority to U.S. provisional patent applications numbered 61/068,763 filed on Mar. 10, 2008 and 61/069,870 filed on Mar. 18, 2008, the disclosures of which are herewith incorporated by reference in their entireties.

FIELD OF THE INVENTION

The present invention relates to medical devices and more particularly to medical devices for joint support.

BACKGROUND

Biomechanical joints, such as the human knee joint, are subject to significant stresses during normal operation. Over time, these stresses can result in deterioration and damage to the joint and its components. In addition, exceptional forces may be applied during an event such as a fall or collision, and may result in sudden damage to the joint. Further, degradation of joint components can result from the action of pathogens, from nutritional deficits, and from various factors associated with aging, for example.

Osteoarthritis is one mechanism resulting in damage to human joints. Often afflicting the middle-aged and elderly, it is nevertheless found patients of all ages. In cases of osteoarthritis, cartilage that normally reduces friction between joint components is degraded or destroyed. A significant increase in frictional forces within the joint can result. Consequently, a victim of osteoarthritis may experience disabling joint pain, or otherwise be limited in operation of the joint in question. Reduced use of the joint can, in some circumstances, lead to atrophy and further degradation of the joint. It is understood that slowing or reversing such degradation is highly desirable.

SUMMARY

Having examined and understood a range of previously available devices, the Applicant has developed a new and important understanding of the problems associated with the prior art and, out of this novel understanding, has developed new and useful solutions and improved devices, including solutions and devices yielding surprising and beneficial results. The invention encompassing these new and useful solutions and improved devices is described below in its various aspects with reference to several exemplary embodiments including a preferred embodiment.

According to one embodiment, the invention includes a joint brace adapted to cantilever said joint so as to place a first surface region of a joint in spaced relation to a second surface region of said joint.

According to a further embodiment, the invention includes a tensile member and a hinge, the tensile member being adapted to support a joint in cantilever so as to relieve pressure between first and second surface portions of the joint, the hinge being adapted to allow an arcuate translation of the first surface with respect to the second surface.

Accordingly a still further embodiment, the invention includes a knee brace including a hinge portion, the hinge portion including first and second interface portions and a third pivotal portion, the first and second interface portions having respective first and second surface regions defining a first plane and a pivotal portion having a third surface region defining a second plane, the first and second planes being disposed in substantially parallel space relation to one another.

These and other advantages and features of the invention will be more readily understood in relation to the following detailed description of the invention, which is provided in conjunction with the accompanying drawings.

It should be noted that, while the various figures show respective aspects of the invention, no one figure is intended to show the entire invention. Rather, the figures together illustrate the invention in its various aspects and principles. As such, it should not be presumed that any particular figure is exclusively related to a discrete aspect or species of the invention. To the contrary, one of skill in the art would appreciate that the figures taken together reflect various embodiments exemplifying the invention.

BRIEF DESCRIPTION OF THE DRAWINGS

FIG. 19 shows, in perspective view, a portion of a joint brace including an arcuate cruciate hinge according to one embodiment of the invention;

FIGS. 20a-20c show, in perspective view, a portion of an arcuate cruciate hinge including a bumper according to one embodiment of the invention;

FIG. 32a shows a portion of a further joint brace illustrating aspects of the invention;

FIG. 32b shows a portion of a hinge device according to certain aspects and embodiments of the invention;

FIGS. 33a-33d show, in various views, a joint brace illustrating aspects of the invention;

FIG. 34a shows a portion of a further joint brace illustrating aspects of the invention;

FIG. 34b shows an adjustable condyle pad system according to certain aspects and embodiments of the invention.

DETAILED DESCRIPTION

The following description is provided to enable any person skilled in the art to make and use the disclosed inventions and sets forth the best modes presently contemplated by the inventor of carrying out his inventions. In the following description, for purposes of explanation, numerous specific details are set forth in order to provide a thorough understanding of the present invention. It will be apparent to one skilled in the art, however, that the present invention may be practiced without these specific details. In other instances, well-known structures and devices are shown in simplified form in order to avoid unnecessarily obscuring the present inventions.

While the following disclosure is made with reference to human joints, and in particular to the human knee joint, it is to be understood that the principles and details of the disclosed invention may also be applied in a wide variety of other circumstances such as may be apparent, or become apparent, to one of ordinary skill in the art (including, for example, the treatment of other human joints such as elbow joints and, in addition, with relation to various non-human applications such as, for example, veterinary applications).

The human knee joint is subject to degradation, injury and/or failure in a variety of modes. In the course of such degradation, and also subsequent to failure, it is often advantageous to provide support to the joint. A variety of external joint support devices have previously been produced. The inventor of the present invention has invented a new and unanticipated external joint support device including a variety of novel and superior features.

Figure 1:
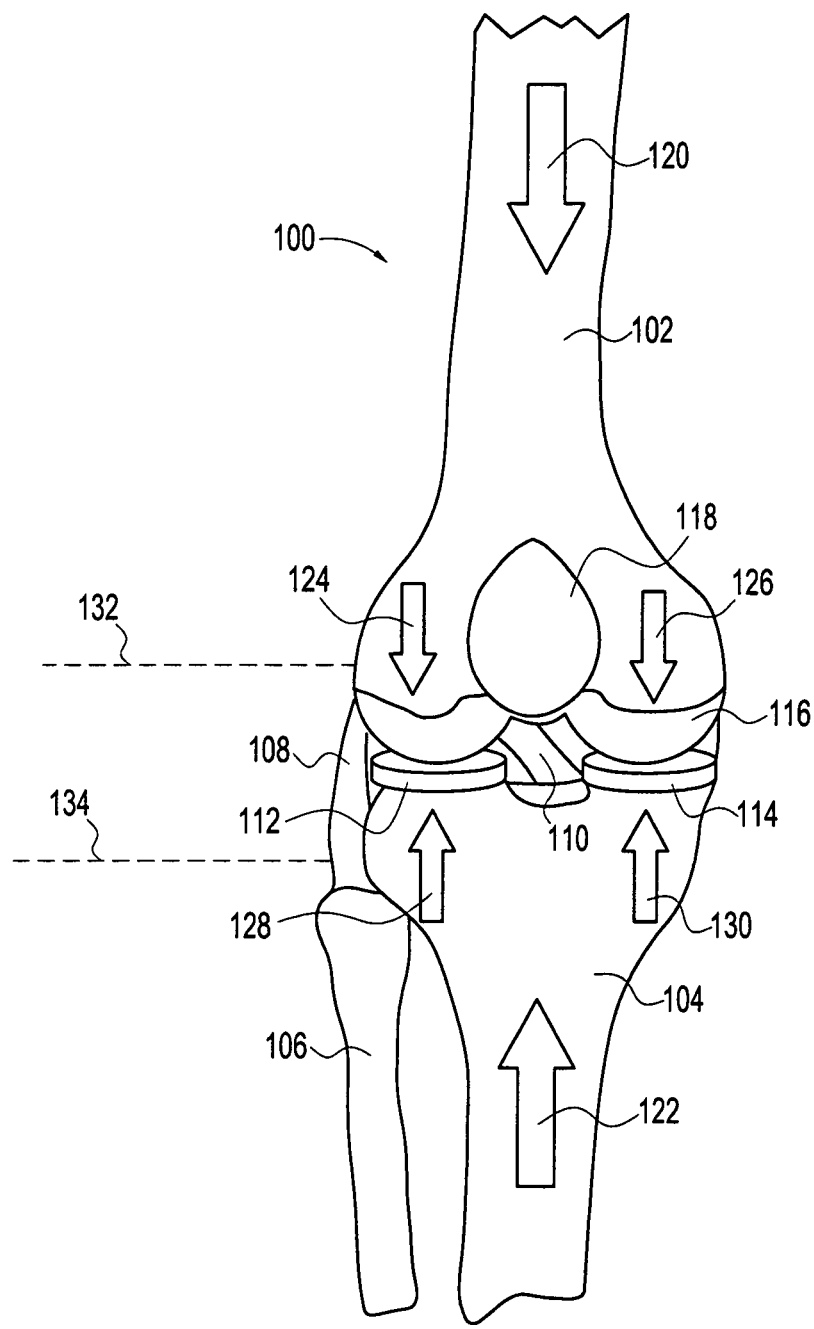
FIG. 1 shows, in schematic form, a portion of an exemplary biomechanical joint in a first configuration including an indication of relevant forces.

FIG. 1 shows a schematic representation of an extended human knee 100 including a portion of a femur 102, a portion of a tibia 104, a portion of a fibula 106, collateral ligaments 108, cruciate ligaments 110, lateral meniscus 112, medial meniscus 114, articular cartilage 116 and patella 118. When supporting a standing subject, a portion of a body weight of the subject is exerted as a gravitational force 120 on the femur 102. This gravitational force 120 is matched by a reactive force 122 exerted through the foot of the subject (not shown) on the tibia 104. Force 120 is distributed across the articular cartilage 116 as indicated by arrows 124, 126. In like fashion, force 122 is distributed across the lateral meniscus 112 and medial meniscus 114 as indicated by arrows 128, 130 respectively. In normal operation, during flexing of the knee joint, the femur 102 is adapted to rotate about a first axis of rotation 132. Substantially simultaneously, the tibia 104 is adapted to rotate about a second axis of rotation 134. To effect these rotations, respective surface regions of the articular cartilage 116 slide across corresponding surface regions of the lateral meniscus 112 and medial meniscus 114.

Various conditions can result in inflammation, damage to or destruction of one or more portions of the knee such as, for example, the meniscae 112, 114 or the articular cartilage 116. Osteoarthritis is one such condition.

In the case of such damage, it may be advantageous to displace the elements of the knee so as to unload one or both of the meniscae 112, 114. In particular, where one meniscus is damaged and the other is in comparatively undamaged condition, a transfer of load from the damaged to the undamaged meniscus is advantageous. Such a transfer of load can be achieved by an application of forces as shown, for example in FIGS. 2 and 3.

Figure 2:
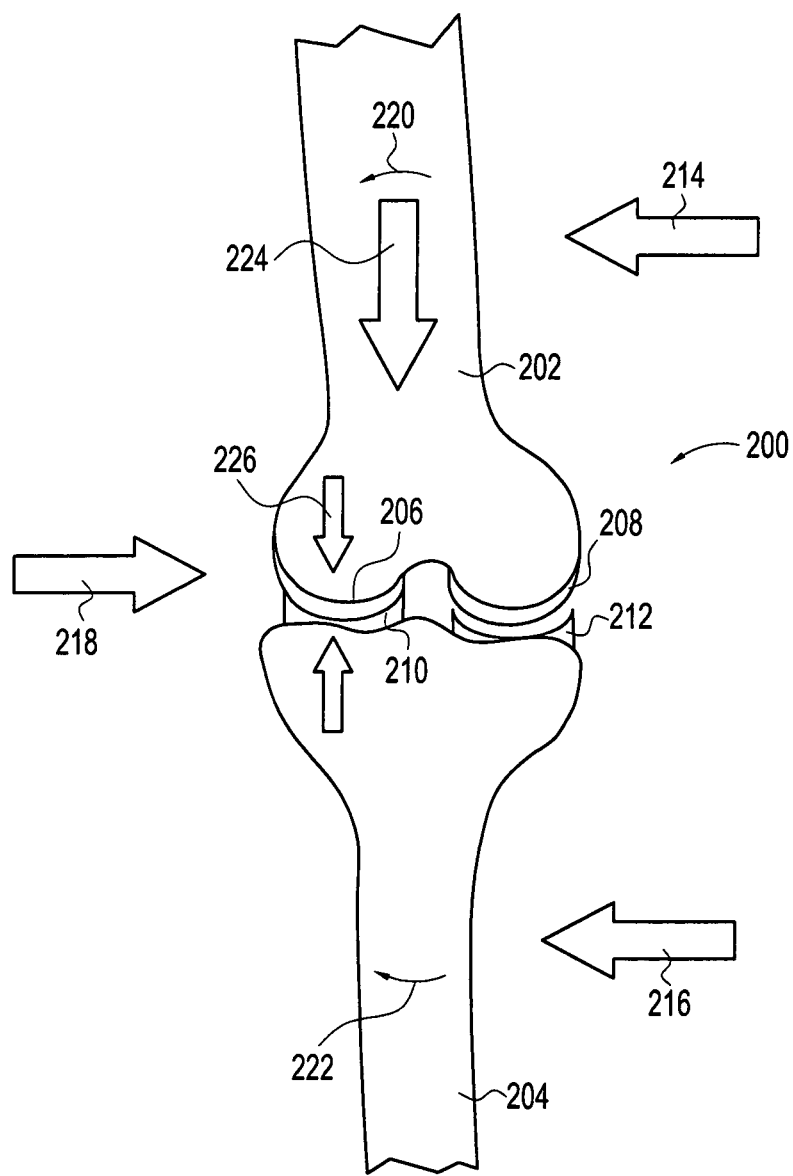
FIG. 2 shows, in schematic form, a portion of an exemplary biomechanical joint in a second configuration including an indication of relevant forces.

FIG. 2 shows, in cross-section, a schematic representation of a portion of a human knee joint 200. The illustrated elements of the knee include a portion of a femur 202, a portion of a tibia 204, first 206 and second 208 regions of articular cartilage and respective portions of a lateral meniscus 210 and a medial meniscus 212. The application of first and second medial forces is illustrated by first and second arrows 214, 216 respectively. The application of an opposing lateral force is illustrated by arrow 218. In response to the applied forces 214, 216 and 218, the femur 202 and tibia 204 experience respective rotations 220, 222 about the interface between cartilage region 206 and meniscus 210. One of skill in the art will appreciate that the effect of forces 214, 216 and 218 is to cantilever articular cartridge region 208, and an adjacent region of femur 202 over medial meniscus 212 and an adjacent region of tibia 204. Consequently, gravitational forces 224 are primarily applied 226 to an interface between articular cartilage region 206 and lateral meniscus 210 while, correspondingly, an interface between cartilage region 208 and meniscus 212 is unloaded.

It should be appreciated that the figures provided herewith are not drawn to scale, and that, for example, the spacing between cartilage region 208 and meniscus 210 may be exaggerated. In addition, in various circumstances one or more of cartilage region 206, 208 and meniscus 210, 212 may be damaged, inflamed or absent.

Figure 3:
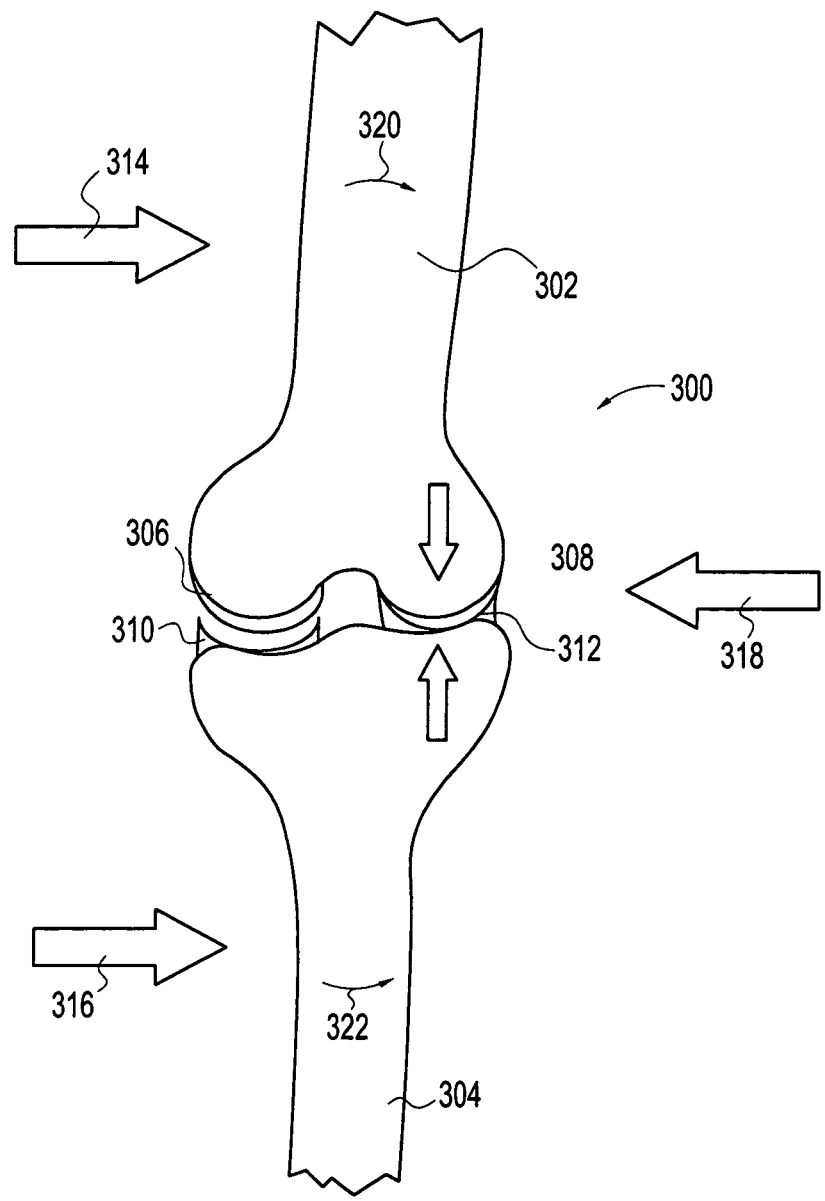
FIG. 3 shows, in schematic form, a portion of an exemplary biomechanical joint in a third configuration, including an indication of relevant forces.

FIG. 3 shows a further schematic cross-section of a knee 300, corresponding to that of FIG. 2, but with the forces reversed. Accordingly, FIG. 3 shows a portion of a femur 302, a portion of a tibia 304, first 306 and second 308 regions of articular cartilage and respective portions of a lateral meniscus 310 and a medial meniscus 312. The application of respective lateral forces is illustrated by first and second arrows 314, 316. The application of an opposing medial force is illustrated by arrow 318. In response to the applied forces 314, 316 and 318, the femur 302 and tibia 304 experience respective rotations 320, 222 about the interface between cartilage region 308 and meniscus 312. Consequently, the interface between articular cartilage region 306 and lateral meniscus 310 is unloaded.

In various circumstances, and according to certain embodiments of the invention, unloading of a cartilage/meniscus interface is effective to reduce pain associated with flexing of joint and/or reduce incremental damage associated with such flexing. Accordingly, in various embodiments, the invention includes an application of forces, as illustrated in FIGS. 2 and 3, including a method of applying such forces that further allows concurrent flexing of the subject biomechanical joint.

Figure 4:
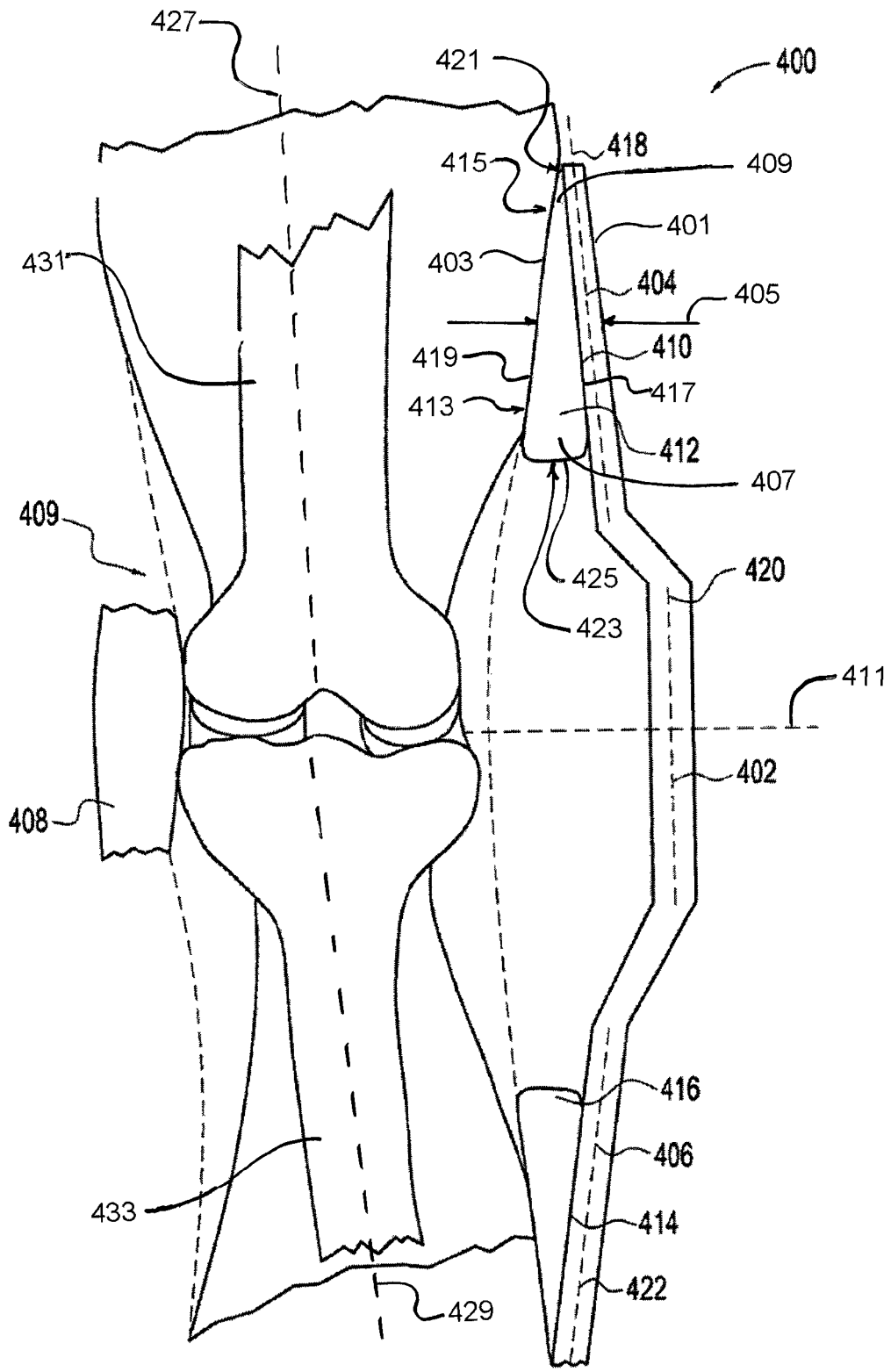
FIG. 4 shows, in schematic form, a portion of an exemplary joint brace in relation to a biomechanical joint.

FIG. 4 shows, in cross-section, a schematic presentation of a portion of an orthotic brace 400 according to one embodiment of the invention. In the illustrated embodiment, the orthotic brace 400 includes a hinge portion 402, a first support portion 404, a second support portion 406 and an opposed portion. In the illustrated embodiment, the opposed portion is shown as a condyle pad 408. The brace 400 is shown positioned adjacent to a cross-section of a portion of a knee 409 of a patient so as to indicate a general arrangement of the brace 400, when in use. As is obvious upon inspection, various details of the knee and of the brace are omitted for clarity.

According to the illustrated embodiment, the first support portion 404 includes a first surface region 410. As illustrated, a first wedge device 412 is disposed between surface region 410 and the leg of the patient. The second support portion 406 includes a second surface region 414. A second wedge device 416 is disposed between surface region 414 and the leg of the patient.

In various embodiments of the invention, as will be described below, apparatus is provided to couple the first 412 and second 416 wedge devices to the opposed portion 408 so as to apply forces, as identified by arrows (214, 216, 218) shown in FIG. 2, to the knee 409.

In various embodiments of the invention, one or more of the wedge devices 412, 416 includes a substantially rigid material. In various embodiments of the invention, one or more of the wedge devices 412, 416 includes a substantially elastic material, e.g., foam, closed-cell foam, open-cell foam, natural polymer, synthetic polymer, natural fiber material, synthetic fiber material, leather, cork, wood, metal, or other materials and combinations thereof. In one embodiment of the invention, the wedge device includes a closed cell polyethylene foam material. In another embodiment of the invention the wedge device includes a closed cell neoprene material.

In a further aspect, according to the illustrated embodiment of the invention, a longitudinal axis 418 of the first support portion 404 is disposed substantially non-coplanar with respect to a longitudinal axis 420 of the hinge portion 402. In a still further aspect according to the illustrated embodiment of the invention a longitudinal axis 422 of the second support portion 406 is also disposed essentially non-coplanar with respect to longitudinal axis 420. In addition, according to one embodiment of the invention, longitudinal axis 422 is disposed essentially non-coplanar with respect to longitudinal axis 418. In another embodiment of the invention, longitudinal axis 422 is disposed substantially coplanar with respect to longitudinal axis 418.

Upon inspection, it is evident from FIG. 4, that the figure illustrates certain aspects of the invention wherein a brace includes a first support 404. The first support 404 is coupled to a second support 406 at a hinge portion 402. The first support 404 includes first 401 and second 403 surfaces. The first and second surfaces are disposed in spaced relation to one another such that the first and second surfaces define a local thickness 405 between them. The local thickness decreases substantially monotonically between a first region 407 proximate to the hinge portion and a second region 409 relatively distal to the hinge portion.

Alternately, one may describe certain aspects of the invention, also in relation to FIG. 4, as a joint brace with a first portion 404 and a second portion 406. The first portion 404 is pivotally coupled to the second portion 406 about an axis of rotation 411. The first portion 404 includes an inner surface 403 and an outer surface 401. The inner surface 403 and outer surface 401 are disposed in spaced relation to one another. The inner surface includes first 413 and second 415 surface regions. The first surface region 413 is disposed relatively proximate to the axis of rotation 411 as compared with the second surface region 415. Accordingly, the second surface region is disposed relatively distal to axis of rotation 411. In certain embodiments, and as illustrated, the inner surface 403 is disposed monotonically closer to the outer surface 401 as measured over a range from the first surface region 413 to the second surface region 415.

FIG. 4 also shows a wedge 412 with a body portion. The body portion has a first surface 417, a second surface 419, and a third surface 425. The first surface 417 and second surface 419 diverge over a range from a first terminal end 421 of the wedge to a second terminal end 423 of the wedge. As illustrated, the wedge is adapted to be disposed between a cuff portion of an orthotic brace and an outer surface of a patient's limb. Also identified are longitudinal axes 427 and 429 of respective bones 431 and 433.

In various embodiments of the invention the brace 400 can be reconfigured and/or worn on a medial side or a lateral side of a right leg or a left leg so as to apply forces similar to those shown in FIGS. 2 and 3 respectively to either the left leg or the right leg of a patient. According to one advantageous aspect of various embodiments, such reconfiguration can be performed quickly and with a minimum of, or no, professional assistance. Thus, in one embodiment of the invention, a single brace may be worn in a variety of positions and orientations.

In certain embodiments of the invention, the condyle pad 408 includes a substantially rigid material. In various embodiments of the invention, the condyle pad 408 includes a substantially elastic material, e.g., foam, closed-cell foam, open-cell foam, natural polymer, synthetic polymer, natural fiber material, synthetic fiber material, leather, cork, wood, metal, or other materials and combinations thereof. In one embodiment of the invention, the condyle pad includes a closed cell polyethylene foam material. In another embodiment of the invention the condyle pad includes a closed cell neoprene material.

According to various embodiments, straps, including, for example, adjustable straps, are provided for coupling the opposed portion 408 to the balance of the brace 400. In various embodiments, the straps include coupling devices including, for example, snaps, buckles, hook and loop material (Velcro®), etc., as known to one of ordinary skill in the art. An exemplary arrangement of such straps is illustrated in FIGS. 5 and 6.

Hinge portion 402 includes, in various embodiments, a wide variety of hinges as known in the art. In particular, a novel arcuate cruciate hinge is advantageously employed. Exemplary hinges are shown, or example, in FIGS. 19, 21 and 24, as discussed below.

Figure 5:
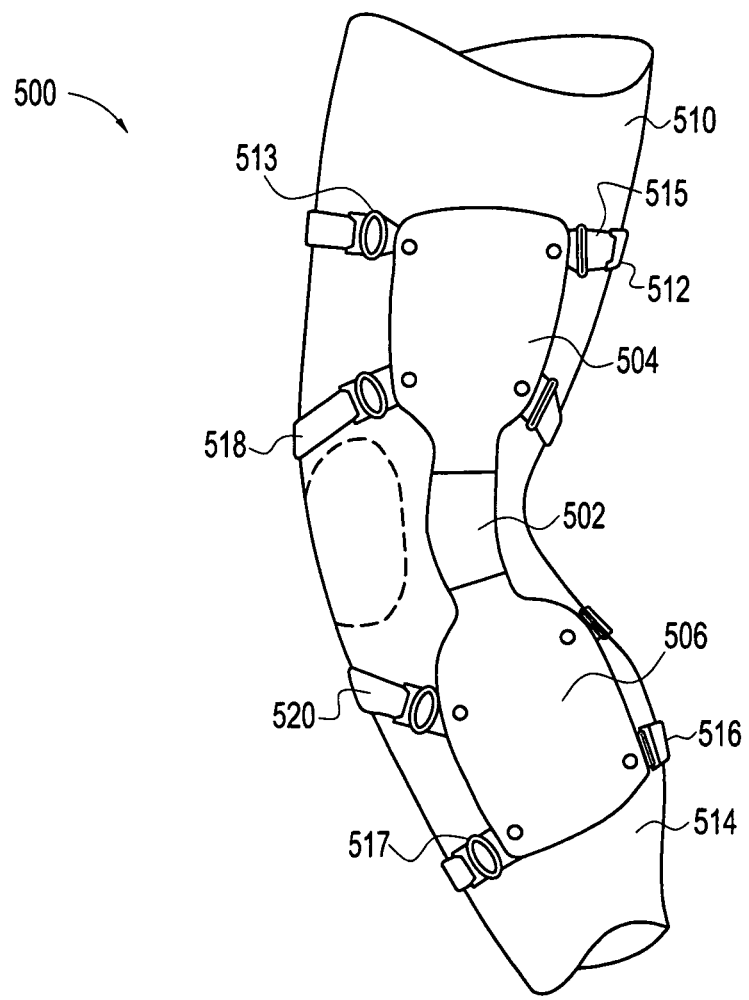
FIG. 5 shows, from one perspective, a portion of an exemplary joint brace according to one embodiment of the invention.
Figure 6:
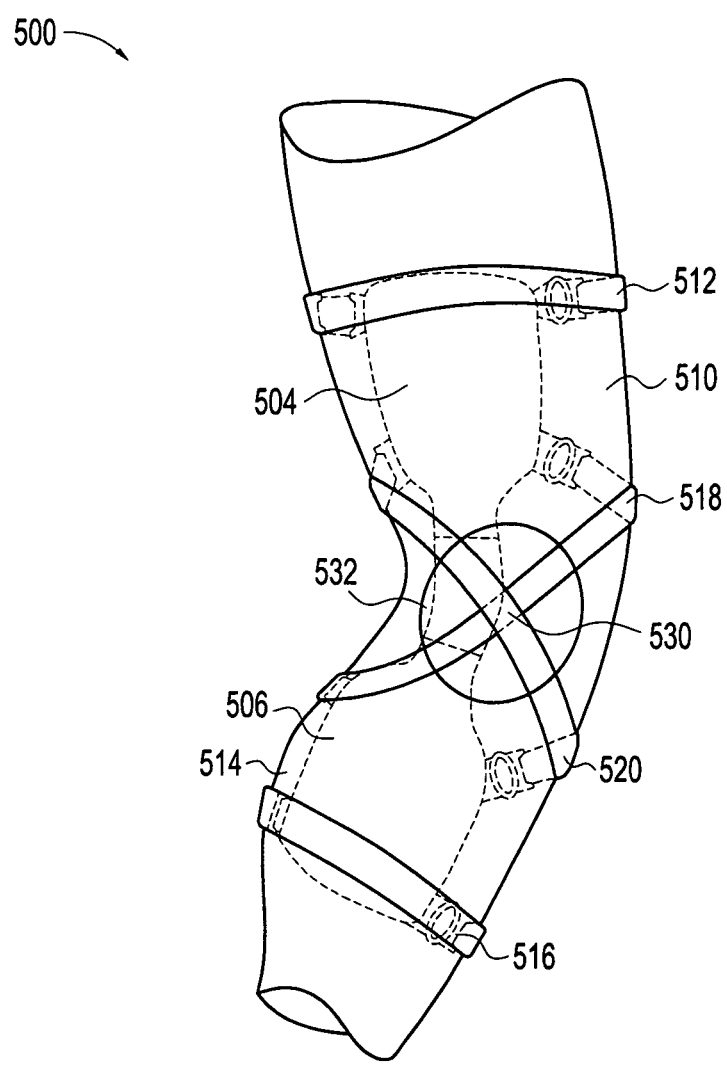
FIG. 6 shows, from an alternative perspective, a further portion of an exemplary joint brace according to one embodiment of the invention.

FIG. 5 shows an aspect of a knee brace 500 according to one embodiment of the invention from an exemplary, a lateral perspective. It should be noted, however, that the knee brace 500 can be arranged and applied so that the view of FIG. 5 represents a view from a medial perspective. This ability to apply an embodiment of the brace laterally or medially represents an advantageous feature of the brace of the present invention. In the illustrated embodiment 500, a first support portion is configured as a first paddle portion 504. A second support portion is configured as a second paddle portion 506. A hinge portion 502 is disposed between paddle portion 504 and paddle portion 506.

As illustrated, paddle portion 504 is held adjacent to a thigh 510 of a patient by a first location strap 512. Paddle portion 506 is held adjacent to a calf 514 of the patient by a second location strap 516. As will be further described in relation to FIG. 6, additional location straps 518, 520 also serve to maintain the position of the knee brace 510 with respect to the patient, as well as to apply forces to the patient's knee.

FIG. 6 shows the knee brace 500 of FIG. 5 from a medial perspective (as noted above, application of the brace so that FIG. 5 presents a lateral perspective is also possible). The first 504 and second 506 paddle portions are shown in broken line, as viewed through the thigh 510 and calf 514 of the patient respectively. Medial portions of the first 512 and second 516 location straps are also visible, as are medial portions of additional location straps 518, 520. In the illustrated embodiment, straps 518 and 520 cross 530 in a region substantially adjacent to a condyle pad 532 and substantially adjacent to the knee joint of the patient.

In the illustrated embodiment, the condyle pad 532 is disposed between the additional location straps 518, 520 and the knee of the patient. In various embodiments of the invention, the location straps 518, 520 are coupled to the condyle pad 532. In one embodiment of the invention, the location straps 518, 520 pass through a portion of the condyle pad 532. According to one embodiment, the location straps 518, 520 are disposed within a slit in a covering or layer of the condyle pad 532.

In one exemplary method for using the joint brace, according to the invention, paddle 504 is positioned adjacent to a thigh 510 of the patient. Strap 512 is fastened around the thigh by coupling the quick release buckle 513. The length of the strap is adjusted by adjusting a hook and loop fastener 515. According the, the strap 512 is rendered snug around the thigh.

In like fashion strap 516 is fastened around the calf 514 of the patient, fastened in place with quick release buckle 517 and adjusted to fit snugly around the calf. Thereafter, straps 518 and 520 are attached using their respective quick release buckles and adjusted to apply a desired force on condyle pad 532 and consequently on the joint of the knee.

According to one embodiment of the invention, straps 518 and 520 are substantially inelastic so that a relatively high force can be applied to the condyle pad. In other embodiments of the invention, straps 518 and 520 have an engineered elasticity, according to the particular application. In another embodiment, a selected elasticity of the condyle pad allows an appropriate force to be conveyed from the substantially inelastic straps 518 and 520 to the condyle of the knee.

In one embodiment the straps 518, 520 include a natural material and in another embodiment the straps 518, 520 include a synthetic material. In still other embodiments of the invention the straps 518, 520 include a combination of one or more materials. In various embodiments, the straps include one or more of a textile material such as, for example, a woven textile material, a knitted textile material, a braided textile material, a non-woven textile material such as a felted material, a molded material, a monofilament textile material, or a combination thereof. In certain examples, the straps include one or more of a natural polymer and a synthetic polymer.

Exemplary natural materials adaptable for use in the invention include, without limitation, wool, cotton, hemp, linen, flax, silk, leather, vulcanized and un-vulcanized natural rubbers and combinations thereof. Exemplary synthetic materials adaptable for use in the invention include, without limitation, polyethylene, polypropylene, polyvinyl chloride, polyamide, polyaramid, polyurethane, polybutylene, neoprene and others as known in the art, alone or in combination. According to various embodiments materials are applied in one or more of solid, layered, fibrous, net/mesh, open cell foam and closed cell foam configurations, and others as known, or as become known, to one of ordinary skill in the art. In still other embodiments, the straps include a metallic material, such as stainless steel, for example, or an inorganic materials such as graphite fiber, glass fiber, nanotube fiber, or other appropriate material.

Figure 7:
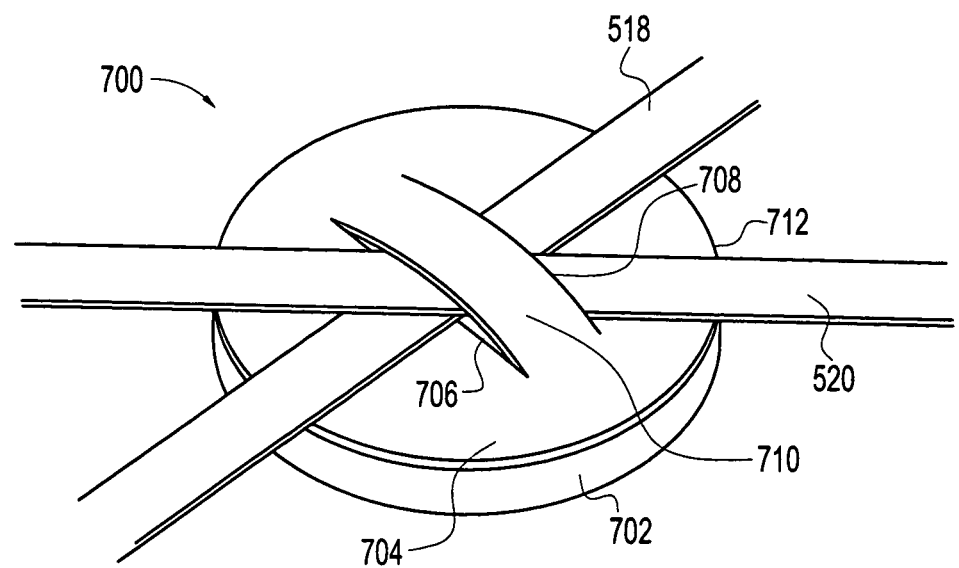
FIG. 7 shows, in perspective view, a portion of an exemplary joint brace including a condyle pad according to one embodiment of the invention.

In the embodiment shown in FIG. 7, a condyle pad 700 includes a first cushioning portion 702 and a second coupling portion 704. In the exemplary embodiment illustrated, the coupling portion 704 includes a layer of material substantially fixedly coupled to the cushioning portion 702. According to one embodiment, first 706 and second 708 slits, or slots, are disposed in the coupling portion 704 as indicated. As per the exemplary embodiment illustrated, the first 706 and second, 708 slits are adapted to receive location straps 518, 520 therethrough so as to effectively couple the condyle pad 720 to location straps 518, 520.

One of skill in the art will appreciate that the illustrated arrangement is exemplary of a wide variety of arrangements by which an appropriate condyle pad 700 can be coupled to location straps 518, 520. Thus in one embodiment of the invention, the cushioning portion 702 and the coupling portion 704 are formed as a single integral unit. In another embodiment of the invention, the coupling portion 704 includes a covering such as, for example, an envelope adapted to receive the cushioning portion 702 within an internal cavity thereof. In one embodiment of the invention, the coupling portion 704 is coupled to the cushioning portion 702 by a permanent adhesive material disposed between the cushioning portion 702 and the coupling portion 704. In still another embodiment of the invention, the cushioning portion 702 is coupled to the coupling portion 704 by an adhesive characteristic or property of one or the other of the cushioning portion 702 or the coupling portion 704. Thus for example in one embodiment of the invention, one or the other of the cushioning portion 702 or the coupling portion 704 is formed by molding or casting in place adjacent to the complementary portion.

Accordingly, in one embodiment of the invention, the cushioning portion 702 is formed by disposing an intrinsically adhesive uncured polymer material adjacent to a surface of the coupling portion 704 and allowing or causing the uncured polymer material to cure so as to substantially permanently adhere the cushioning portion 702 to the coupling portion 704. In one such embodiment of the invention, a barrier layer of material is disposed between the coupling portion 704 and the cushioning portion 702 so as to maintain an open region underneath a strap portion 710 of the coupling portion 704, and consequently an open passageway adapted to receive location straps 518, 520 between slit 706 and 708.

In a further embodiment of the invention, cushioning portion 702 is substantially removably coupled to coupling portion 704 by a fastening device such as, for example, a removable adhesive, a hook and loop fastener device, a snap fastener device, a button device, a toggle device, a rivet device, a zipper device, or any other appropriate fastening device as known in the art.

In one embodiment of the invention, the location straps 518, 520 are adapted to be disposed in crossed relation to one another such that an intersection between the two straps is disposed substantially beneath or within strap portion 710. In another embodiment of the invention, an intersection between the two location straps 518, 520 is adapted to be disposed substantially adjacent to the strap portion 710. In still another embodiment of the invention, the intersection between the two location straps 518, 520 is adapted to be disposed partially beneath or within the strap portion 710.

Figure 8:
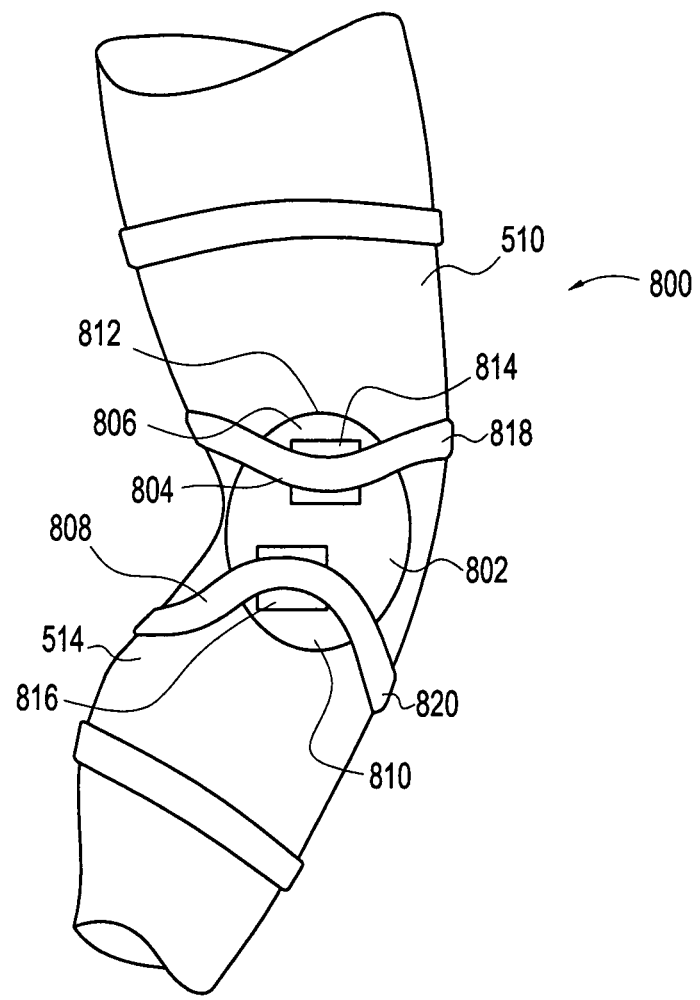
FIG. 8 shows, in perspective view, a portion of an exemplary joint brace according to one embodiment of the invention.

According to one embodiment of the invention, as illustrated, a perimeter 712 of the condyle pad 700 includes a substantially circular portion. In other embodiments of the invention, a perimeter of the condyle pad includes any appropriate configuration including, for example, a polygonal portion such as for example a triangular portion, a rectangular portion, a pentagonal portion, a hexagonal portion, a heptagonal portion, an octagonal portion, etc. FIG. 8 shows an alternative condyle pad arrangement.

FIG. 8 shows a portion of an embodiment of the invention 800 including an exemplary condyle pad 802. In the illustrated embodiment 800, first and second location straps 818, 820 are adapted to be disposed around a thigh 510 and calf 514 of a patient respectively. In contrast to the embodiments illustrated at FIG. 6 and FIG. 7, the location straps 818, 820 are adapted to be disposed in proximate relation to one another without intersecting one another. Accordingly, as shown, in one embodiment location strap 818 is arranged so as to include a first arcuate region 804 or angular region disposed adjacent to an upper region 806 of the condyle pad 802. Location strap 820 is arranged so as to include a second arcuate region 808 or angler region disposed adjacent to a lower region 810 the condyle pad 802.

According to one embodiment, as illustrated, the condyle pad 802 includes a substantially elliptical perimeter 812. As discussed above, however, other configurations of the perimeter are within the scope of the invention. In another aspect of one embodiment, the condyle pad 802 includes one or more of first 814 and second 816 fastening devices disposed at respective surface regions of the condyle pad 802. The fastening devices 814, 816 are adapted to establish a more or less permanent fixed spatial relationship between the condyle pad 802 and the location straps 818, 820 respectively. Accordingly, in one embodiment of the invention, the first and second fastening devices 814, 816 include respective portions of hook and loop fasteners. In another embodiment of the invention, the first and second fastening devices 814, 816 include respective portions of adhesive polymer material. In still another embodiment of the invention the first and second fastening devices 814, 816 include respective portions of adherent polymer material, and in still other embodiments of the invention, the first and second fastening devices 814, 816 include respective mechanical fasteners such as, for example, hook and eye fasteners, snap fasteners, toggle fasteners, button and buttonhole fasteners, rivet fasteners, button and keyhole fasteners, and other such fasteners as known in the art, including combinations thereof.

Figure 9:
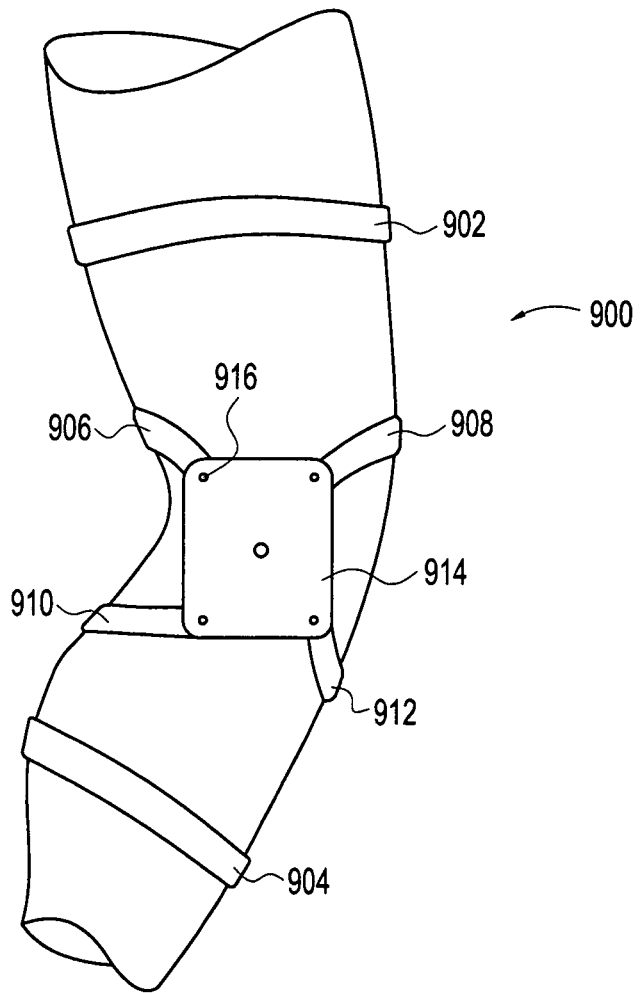
FIG. 9 shows, in perspective view, a portion of an exemplary joint brace according to a further embodiment of the invention.

FIG. 9 shows a portion of a joint brace 900 according to a further embodiment of the invention. The joint brace 900 includes location straps 902 and 904 adapted to be disposed adjacent to a thigh and a calf of a patient respectfully. Additional location straps 906, 908, 910, 912 are adapted to be coupled, for example, to a condyle pad device 914 at respective corners thereof. According to one exemplary embodiment, as illustrated, the coupling between the location strap 906 and the condyle pad device 914 includes a fastener device 916. In one embodiment of the invention, the fastener device 916 provides a pivotal coupling between the location strap 906 and the condyle pad device 914.

Figure 10:
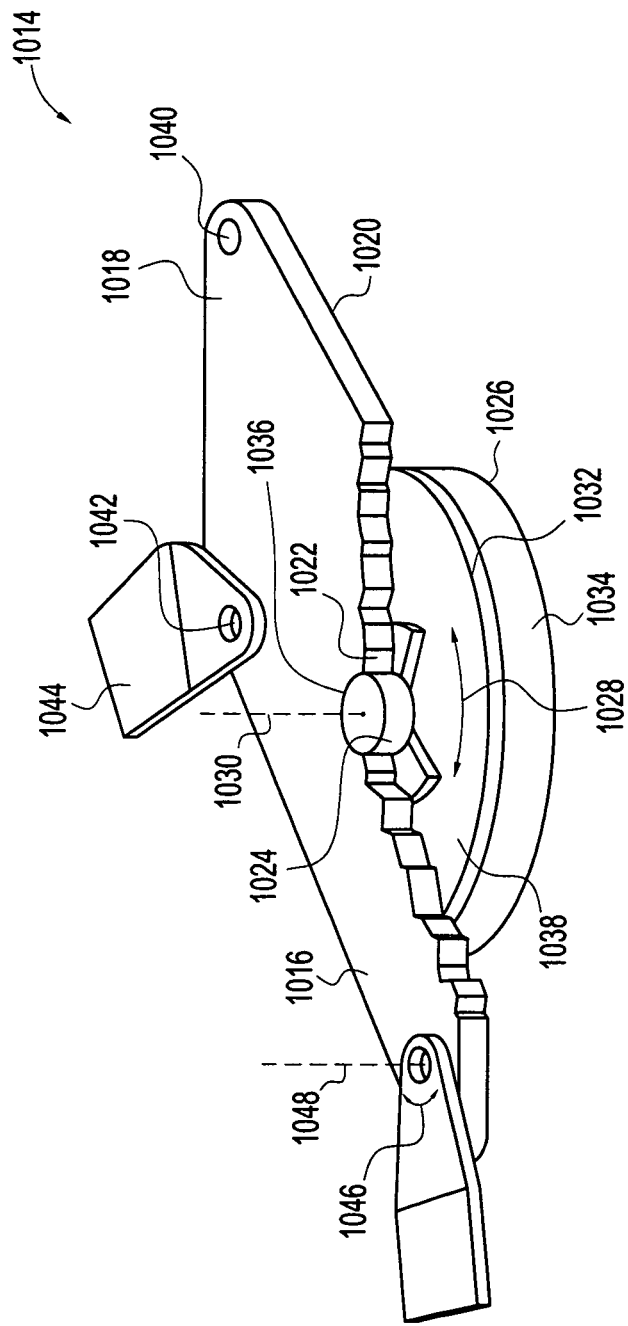
FIG. 10 shows, in cutaway perspective view, a portion of an exemplary joint brace including a condyle pad assembly according to one embodiment of the invention.

FIG. 10 shows, in cutaway perspective view, an exemplary condyle pad device 1014 according to one embodiment of the invention. In the illustrated embodiment, the condyle pad device 1014 includes a structural member 1016 such as, for example, a substantially rigid plate. In the illustrated embodiment, the structural number 1016 includes first 1018 and second 1020 surface regions disposed in substantially parallel spaced relation to one another. A further surface region 1022 disposed between the first 1018 and second 1020 surface regions defines a through-hole adapted to receive a shaft member 1024 therethrough.

In one embodiment, as shown, the shaft member 1024 is adapted to support a pad portion 1026 of the condyle pad device 1014 in pivotally coupled relation to the structural member 1016. Accordingly, in one embodiment of the invention, the pad portion 1026 is adapted to pivot 1028 about a longitudinal axis 1030 of the shaft member 1024. To facilitate this motion, in one embodiment of the invention, the pad portion 1026 includes a first substantially rigid support portion 1032 and a second substantially elastic cushion portion 1034. In the illustrated embodiment, a bearing device such as, for example, a washer is disposed between the structural member 1016 and the pad portion 1026 so as to further facilitate the pivotal motion 1028.

In the illustrated embodiment, the shaft portion 1024 includes a head 1036 to retain the shaft member 1024 within the through hole. A creative practitioner of ordinary skill in the art will appreciate that a wide variety of alternative fastening arrangements fall within the scope of the invention, and that appropriate fastening arrangement is to be chosen according to the requirements of a particular therapeutic application.

In one embodiment of the invention, surface region 1022 includes a plurality of internal threads and shaft member 1024 includes a corresponding plurality of external threads. In such an embodiment, a rotation of the shaft member 1024 by, for example, a rotation of a knob (not shown) provided in place of head 1036 serves to adjust a distance between a surface region 1038 of the rigid support portion 1032 and surface region 1020 of the structural member 1016. According to certain aspects of the invention, this adjustment distance is adapted to provide a corresponding adjustment of a force shown, for example as force 218 in FIG. 2.

In still another embodiment of the invention, one or more spacers, shims or wedges are used with a joint brace to allow for adjustment of a cushioning pad of the device. For example, referring again to FIG. 10, in one embodiment of the invention a plurality of condyle pad of different thicknesses can be provided with a particular brace. Depending on the requirements of a particular patient, a treating practitioner, or the patient him or herself, can select and install the appropriate one of the several pads provided.

In a further embodiment of the invention a single pad is provided, and a plurality of spacers are provided with the brace. Accordingly, depending on the requirements of the patient, one or more of the spacers can be installed between surface 1038 and surface 1020. Thus, for example, the illustrated washer, may provide one or more of a rotary bearing function and a spacing function. It should be noted that spacers of different thicknesses can be provided for use alone or in combination so that an appropriate combination of spacers can provide a wide variety of possible spacings.

In other embodiments, spacers may be wedge-shaped so as to allow an adjustable insertion of a spacer between exemplary supporting surfaces such as 1020 and 1038. In certain embodiments, the spacers include an adhesive and/or adherent surface feature. Thus, for example, a spacer may be inserted between supporting surfaces and tend to remain in place once installed. In certain embodiments, a spacer includes a pre-applied adhesive material on a surface thereof and a release paper adapted to be removed prior to use of the spacers so as to expose the otherwise protected adhesive material. In still another example, the spacer includes a hook and loop fastener feature adapted to hold it in place between a supporting surface of the condyle pad and a backplate.

As shown in the illustrated embodiment, structural member 1016 also includes a further plurality of through holes, e.g., 1040. The further plurality of through-holes are adapted to receive respective fastener devices, e.g., 1042 so as to couple a corresponding plurality of location straps 1044 to the structural member 1016. In various embodiments, the fastener devices include one or more of a rivet, a screw, a nut and bolt, a roll pin, a shaft and cotter pin, a shaft and crown washer, or any other appropriate fastening device such as would be known to the creative practitioner of ordinary skill in the art. According to one embodiment of the invention, the combination of through-hole, e.g., 1040 and fastener, e.g., 1042 is adapted to provide a pivotal coupling 1046 about a longitudinal axis 1048 of the corresponding through-hole. In one embodiment of the invention, the location strap, e.g., 1044 further includes a flange portion 1050 adapted to provide a robust pivotal coupling between the location strap 1044 and the structural member 1016.

Figure 11:
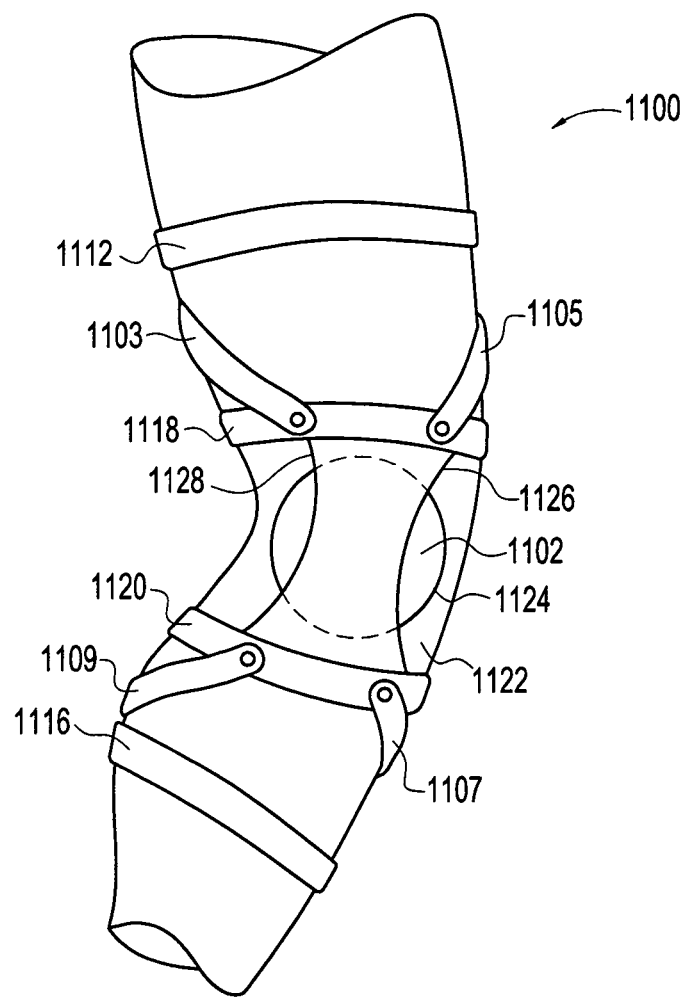
FIG. 11 shows, in perspective view, a portion of a further exemplary joint brace according to one embodiment of the invention.

FIG. 11 shows a portion of a joint brace 1100 according to a further embodiment of the invention. The joint brace 1100 is presented in and orientation adapted to show a condyle pad 1102. Also visible are location straps 1112, 1116, 1118 and 1120. In the illustrated embodiment, a bridge element 1122 is disposed between, and coupled to, location straps 1118 and 1120 respectively. In addition, according to one embodiment of the invention, bridge element 1122 is disposed adjacent to, and coupled to, a condyle pad 1102. Also shown are first 1103, second 1105, third 1107 and fourth 1109 tensile members adapted to apply tensile forces to the bridge element 1122, and consequently to the condyle pad 1102. The resulting forces on the condyle pad apply a force to the knee joint corresponding to, e.g., force 218 as shown in FIG. 2.

In one exemplary embodiment, the bridge element 1122 includes a substantially elastic material. In another exemplary embodiment the bridge element 1122 includes a substantially inelastic material. In various embodiments, a material of the bridge element 1122 includes a natural material and in another embodiment, the bridge element 1122 includes a synthetic material. In still other embodiments of the invention the bridge element 1122 includes a combination of one or more of the foregoing materials. In various embodiments, the bridge element includes one or more of a textile material such as, for example, a woven textile material, a knitted textile material, a braided textile material, a non-woven textile material such as a felted material, a molded material, a monofilament textile material, or a combination thereof. In certain examples, the bridge element 1122 includes one or more of a natural polymer and a synthetic polymer.

Exemplary natural materials adaptable for use in the invention include, without limitation, wool, cotton, hemp, linen, flax, silk, leather, vulcanized and un-vulcanized natural rubbers and combinations thereof. Exemplary synthetic materials adaptable for use in the invention include, without limitation, polyethylene, polypropylene, polyvinyl chloride, polyamide, polyaramid, polyurethane, polybutylene, neoprene and others as known in the art, alone or in combination. According to various embodiments materials are applied in one or more of solid, layered, fibrous, net/mesh, open cell foam and closed cell foam configurations, and others as known, or as become known, to one of ordinary skill in the art.

According to one embodiment of the invention bridge element 1122 is a discrete device adapted to be permanently or removably coupled to one or more of location straps 1118, 1120 using any appropriate method as known to one of ordinary skill in the art. Accordingly, in exemplary embodiments, bridge element 1122 is coupled to location strap 1118 by one or more of textile stitches, chemical adhesive bonding and welding, such as one or more of thermal welding, ultrasonic welding and spot welding, for example. In other embodiments of the invention, bridge element 1122 is coupled to location strap 1118 by a fastening device such as, for example, a removable adhesive, and adherent polymer device, a hook and loop fastener device, a snap fastener device, a toggle device, a rivet device, a zipper device, a snap fastener device, a toggle fastener device, a button and buttonhole device, a button and keyhole fastener device, or any other appropriate fastener device as known in the art.

In still another embodiment of the invention, bridge element 1122 is integrally formed with one or more of location straps 1118, 1120. Accordingly, in one embodiment of the invention, location straps 1118 and 1120 and bridge element 1122 include a single, integrally formed unit such as, for example, and integrally molded device including molded closed cell foam neoprene device, including a textile layer such as a woven polyamide textile layer. In still another embodiment of the invention, location strap 1118 and 1120 and bridge element 1122 include woven textile location straps 1118 and 1120 and a woven bridge element 1122 woven as a single unit between the textile location straps.

According to various embodiments of the invention, condyle pad 1102 is substantially permanently or removably coupled to bridge element 1122. Thus, in one embodiment, condyle pad 1102 is adapted to be coupled at a surface region thereof to a corresponding surface region of bridge element 1122. According to various embodiments of the invention bridge element 1122 is coupled to condyle pad 1102 by one or more of textile stitches, chemical adhesive bonding, welding, such as one or more of thermal welding, ultrasonic welding and spot welding, for example. In other embodiments of the invention, bridge element 1122 is coupled to condyle pad 1102 by a fastening device such as, for example, a removable adhesive, and adherent polymer device, a hook and loop fastener device, a snap fastener device, a toggle device, a rivet device, a zipper device, a snap fastener device, a toggle fastener device, a button and buttonhole device, a rivet fastener device, a button and keyhole fastener device, or any other appropriate fastener device as known in the art.

In still other embodiments of the invention, the condyle pad 1102 and bridge element 1122 are formed as a single integral device. Accordingly, in one embodiment of the invention, the bridge element 1122 and condyle pad 1102 are formed as a single molded polymer device. According to one embodiment of the invention, the bridge element 1122 and condyle pad 1102 are formed as a single device including a first molded closed cell neoprene material and a second polymer fiber textile material such as, for example, a woven polyamide or polyaramid material or a knitted polyamide or polyaramid material. In another embodiment of the invention, bridge element 1122 and condyle pad 1102 are formed as a single device including a molded polymer device such as, for example, a molded polyethylene device or a molded polyvinyl chloride device. In various embodiments, the molded polymer device includes a portion having a flexible region and a gas-filled interior cavity. According to one embodiment, the flexible region and gas filled interior cavity form a cushioned condyle pad region. In one embodiment of the invention, the cushioned condyle pad region includes a plurality of discrete or connected gas filled interior cavities.

As discussed above in relation to other exemplary embodiments of the invention, a perimeter 1124 of the condyle pad 1102 may be arranged in any configuration appropriate to a particular application, as determined by one of ordinary skill in the art. In like fashion, although the edges 1126, 1128 of the bridge element 1122 are shown to have arcuate form, other configurations, appropriate to particular needed applications, are also within the scope of the invention.

Figure 12:
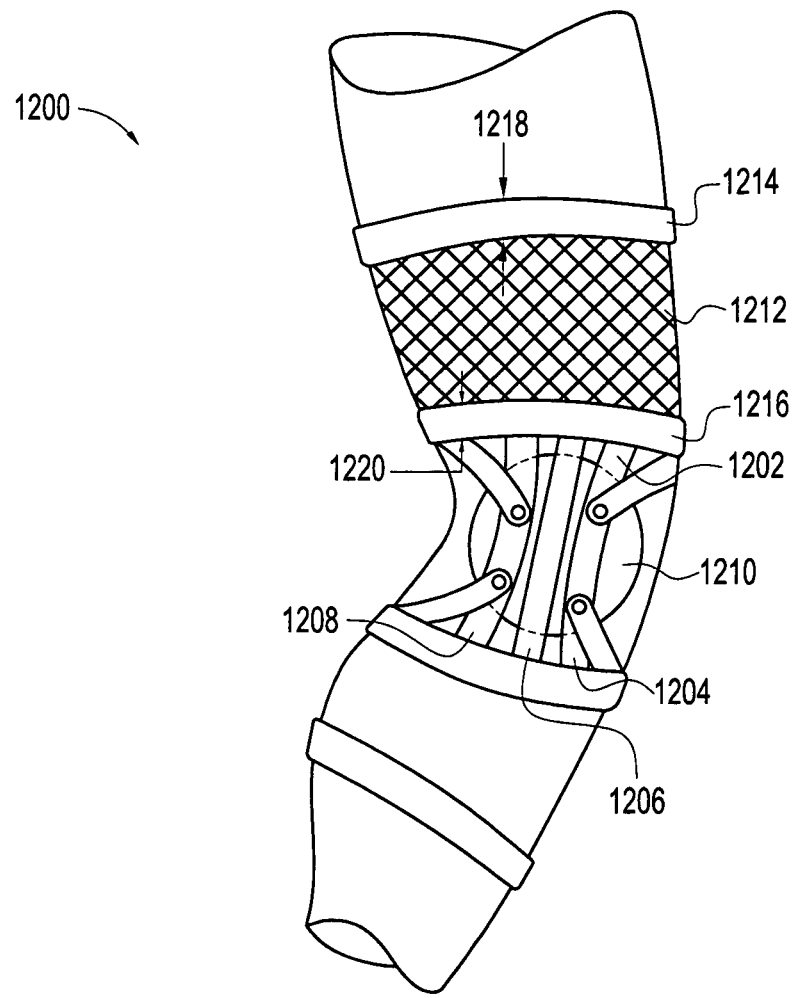
FIG. 12 shows, in perspective view, a portion of still another exemplary joint brace according to another embodiment of the invention.

FIG. 12 shows a further exemplary embodiment of the invention 1200 including a bridge element 1202 having a plurality of sub-elements, 1204, 1206, 1208. A creative practitioner of ordinary skill in the art will appreciate that the three sub-elements illustrated in FIG. 12 are merely exemplary of the many possible configurations, e.g., 2, 4, 5, 6, 7, 8, 9, . . . sub-elements that a creative practitioner would employ as appropriate to various circumstances, all of which fall within the scope of the invention as disclosed herewith. In like fashion, various configurations of sub-element are appropriately combined with various configurations of discrete or integral condyle pad 1210, as previously discussed. In embodiment 1200 of FIG. 12 a plurality of tensile members, corresponding to tensile members 1103, 1105, 1107 and 1109 of FIG. 11 are provided to apply tensile forces to the bridge element 1202.

In a further aspect of the embodiment illustrated in FIG. 12, a coupling device 1212 is provided between first 1214 and second 1216 location straps. In the illustrated embodiment, the coupling device 1212 include a plurality of substantially elastic longitudinal members arranged in a mesh or net. In other embodiments, the coupling device 1212 includes, for example, one or more of a woven textile material, a nonwoven textile material, a knitted textile material, a polymer foam material, a polymer sheet material or any other appropriate elastic or inelastic structural material, as would be determined appropriate to particular circumstances by a creative practitioner of ordinary skill in the art. It should be noted that while, in some embodiments, the location straps 1214, 1216 of embodiment 1200 may be substantially equal in width 1218, 1220, in other embodiments, such will not be the case. In some embodiments, location strap 1214 will be wider than location strap 1216 and, in other embodiments, location strap 1214 will be narrower than location strap 1216.

Figure 13:
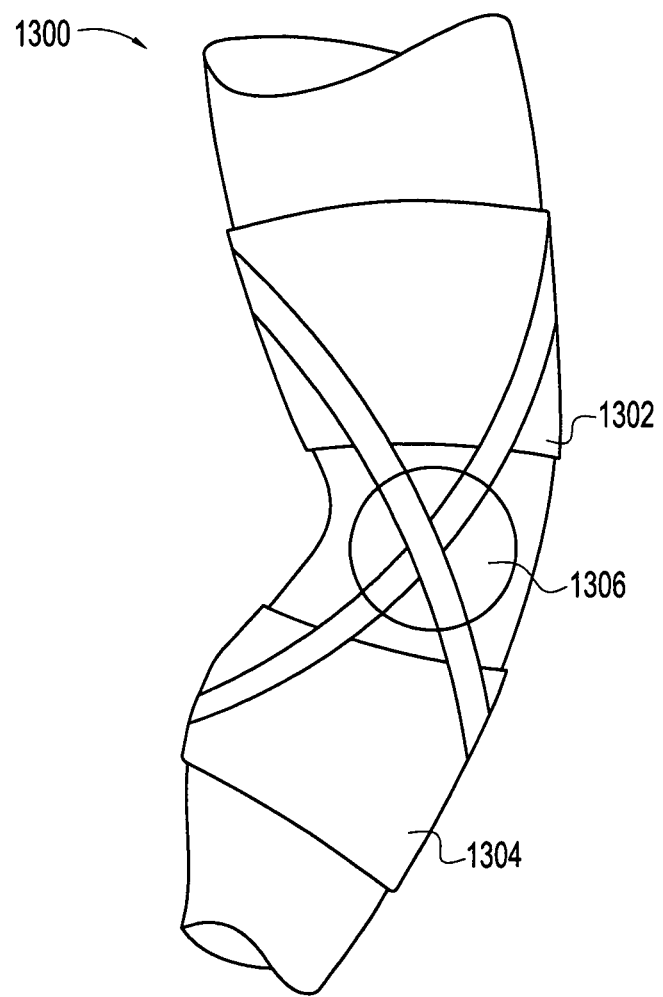
FIG. 13 shows, in perspective view, a portion of an exemplary joint brace according to a still further embodiment of the invention.

FIG. 13 shows a still further exemplary embodiment of the invention 1300 including an upper location cuff 1302 and a lower location cuff 1304. In various embodiments, the upper and lower location cuffs 1302, 1304 include, for example, a substantially elastic material such as, for example, closed cell neoprene foam sheet. In one embodiment of the invention, the upper and lower location cuffs 1302, 1304 include longitudinal portions adapted to be wrapped around respective regions of a patient's leg and held in place by, for example, respective hook and loop fastener devices. In various embodiments, tensile members, as shown, are disposed within or coupled to surfaces of the cuff to apply appropriate forces, as discussed above, to a condyle pad 1306.

One of skill in the art will appreciate that a wide variety of textile materials are adaptable for use in various embodiments of the invention. Thus, in one embodiment, an exemplary cuff 1302 includes a woven textile material. In another embodiment of the invention cuff 1302 includes a knitted textile material and in another embodiment of the invention, cuff 1302 includes a non-woven textile material.

In various embodiments, the textile material includes one or more synthetic material such as, for example polyamide (Nylon®), polyolefin, polyacetate, polyethylene, polypropylene, polyaramid (Kevlar®), polyester. In still other embodiments, the textile material includes one or more fibrous elastomeric materials such as, for example, polyurethane. In certain embodiments, the above and other materials are combined with, or substituted by, natural polymer materials such as, for example, cotton, wool, flax, hemp, and bamboo, among others, or by a regenerated naturally occurring polymer such as, for example regenerated cellulosic fiber (e.g. Rayon). In still other embodiments of the invention, the cuff includes a natural or synthetic leather or a natural or synthetic rubber.

In certain embodiments of the invention, the cuff 1302 includes a material molded or extruded into a sheet form such as, for example, polyethylene, polypropylene, polyamide, polyaramid, or polyurethane for example. In certain embodiments, the cuff 1302 includes an open cell foam or a close cell foam such as, for example, a neoprene foam material. Thus, in one exemplary embodiment, the cuff includes a woven nylon textile material bonded to a close neoprene foam.

In embodiment 1302, as illustrated, cuffs 3002 and 3004 are wrapped around patient's leg and retained in place by a fastening device. In one embodiment, the fastening device includes a hook and loop fastener such as Velcro® or an equivalent. In another embodiment, the fastening device includes a snap fastener. In still another embodiment, the fastening device includes one or more of a button fastener, a zipper fastener, a toggle fastener, and any of a wide variety of adhesive fasteners. Included among such adhesive fasteners are reusable and not reusable adhesive tape fasteners adherent polymer fasteners and nanotechnology (synthetic gecko skin fasteners). What skill in the art will appreciate that a wide variety of fasteners and arrangements are employed as appropriate to retain respect of embodiments of the strap in position is shown.

Figure 14A:
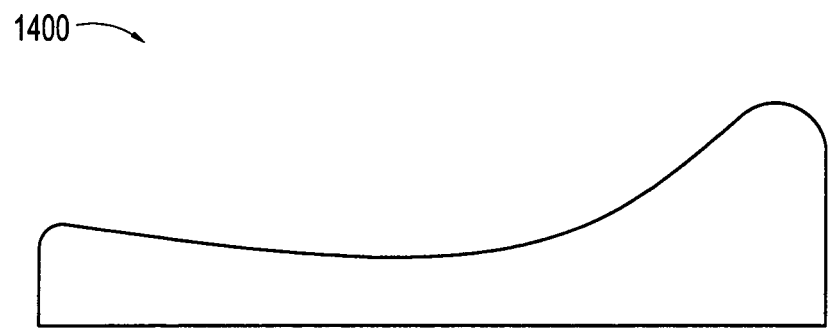
FIGS. 14a and 14b show alternative views of a condyle pad according to one embodiment of the invention.

FIG. 14*a* shows, in cross-section, a condyle pad 1400 according to one embodiment of the invention. In one embodiment, the condyle pad is formed of a polyethylene material having a durometer appropriate to apply a requisite force (e.g. force 218 as shown in FIG. 2 of FIG. 2) without harming or irritating a patient's joint or the flesh adjacent to the joint.

Figure 14B:
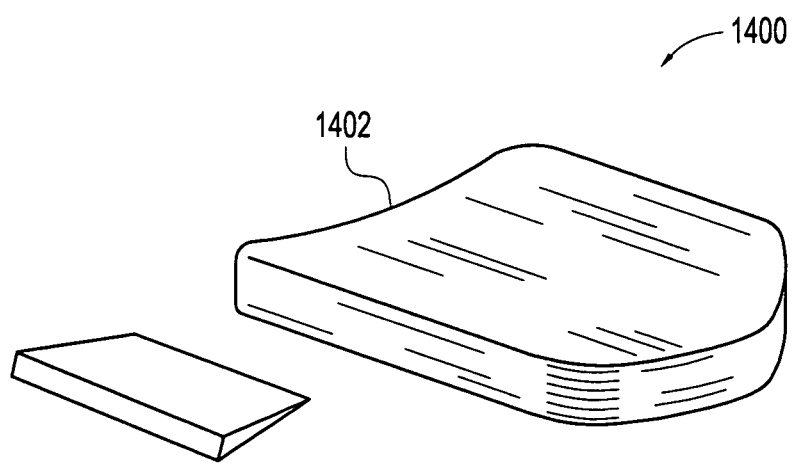

FIG. 14*b* shows condyle pad 1400 in perspective view. As shown, the condyle pad 1400 includes a concave surface region 1402 adapted to receive the subject joint adjacent thereto. In one embodiment, the condyle pad 1400 includes a closed cell foam polyethylene material.

In various embodiments, the condyle pad may include a plurality of materials. For example in one embodiment, a condyle pad includes a plurality of layers of various materials. In certain embodiments, the various layers of materials have respective differing durometers. Thus in one embodiment, a layer of relatively inelastic durometer is provided comparatively distal with respect to a knee joint where as a layer of relatively inelastic durometer is provided comparatively proximate to the knee joint. In still another embodiment, a stuffing material of relatively low durometer is provided within a cavity of a condyle pad, the condyle pad including a substantially flexible external region or cover.

In a joint brace according to one embodiment of the invention, a plurality of condyle pads of differing thicknesses are provided where one or another of the plurality of condyle pads is adapted for use with the joint brace at particular time. Thus, in some circumstances a relatively thick condyle pad will be beneficially applied to increase an applied cantilever force or to provide additional cushioning. In another circumstance, a relatively in condyle pad will be beneficially applied. In still other circumstances a condyle pad assembly includes a location or cavity where an adjusting device such as, for example a wedge-shaped shim may be applied. Thus in some embodiments, a shim is applied between a backing and a cushion of a condyle pad so as to adjust an effective thickness of the condyle pad assembly.

Referring again to FIG. 5, the inventor notes that linking device 502 is provided between paddle portions 504 and 506. Further detail will now be provided with respect to exemplary linking devices.

Figure 15:
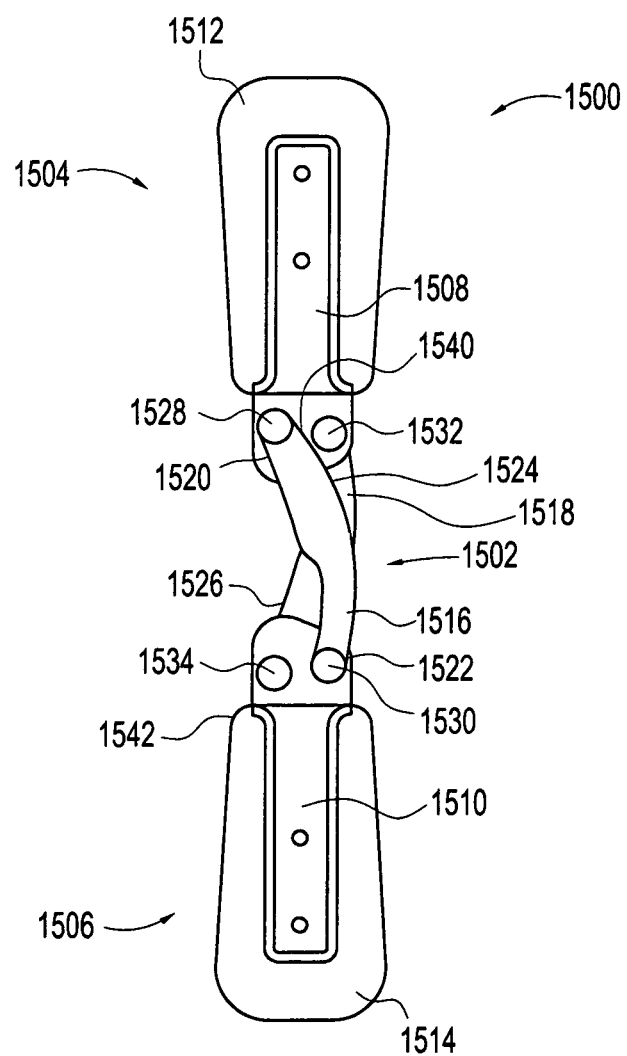
FIG. 15 shows a hinge assembly adaptable for use in a joint brace according to one embodiment of the invention.

FIG. 15 shows an exemplary linking device 1500 including an arcuate cruciate hinge 1502 according to one embodiment of the invention. The linking device 1500 includes first 1504 and second 1506 support portions as well as exemplary first 1508 and second 1510 flange members and paddle portions 1512, 1514 coupled to the flange members respectively. Cruciate hinge 1502 is formed by pivotally coupling first 1516 and second 1518 supporting members between the flange members 1508, 1510. Accordingly, supporting member 1516 is pivotally coupled at a first end 1520 to flange member 1508 and at a second end 1522 to flange member 1510. Supporting member 1518 is pivotally coupled at a first end 1524 to flange member 1508 and at a second end 1526 to flange member 1510. In the illustrated embodiment, the pivotal couplings are formed with respective rivet fasteners 1528, 1530, 1532 and 1534. As will be discussed in additional detail below, one of skill in the art will appreciate that a wide variety of other fastening devices are employed in alternative embodiments of the invention.

In operation flange member 1508 is adapted to pivot around an axis of rotation 1540 disposed between the centers of fasteners 1528 and 1532. Concurrently, flange member 1510 is adapted to pivot around and axis of rotation 1542 disposed between the centers of fasteners 1530 and 1534. In a first mode of operation, concurrently with the respective rotations of flanges 1528 and 1532 about axes 1540 and 1542, axis 1540 remains fixed at a single point in space while axis 1542 traverses a circular arc centered at axis 1540. In a second mode of operation axis 1542 remains fixed in a single point in space while axis 1540 traverses a circular arc centered at axis 1542. In still another mode of operation, axes 1540 and 1542 both remain substantially fixed at a single point in space while flange members 1508 and 1510 rotate about axes 1540 and 1542 respectively.

In still further modes of operation, the motions described above are executed concurrently to produce linear combinations of the motions described above. Advantageously, for a properly configured and positioned device, the modes of operation described above are well adapted to maintain the axes 1540 and 1542 in substantially constant and coincident relation with joint axes 132 and 134 (as illustrated and described above in relation to FIG. 1). As discussed above in relation to FIG. 1, the femur and tibia tend to rotate about discrete axes 132, 134 that are generally parallel to one another but separated in space. Consequently, in order to support the joint with a minimum of additional stresses, the cruciate hinge 1502 is adapted to rotate about axes 132 and 134.

Figure 16:
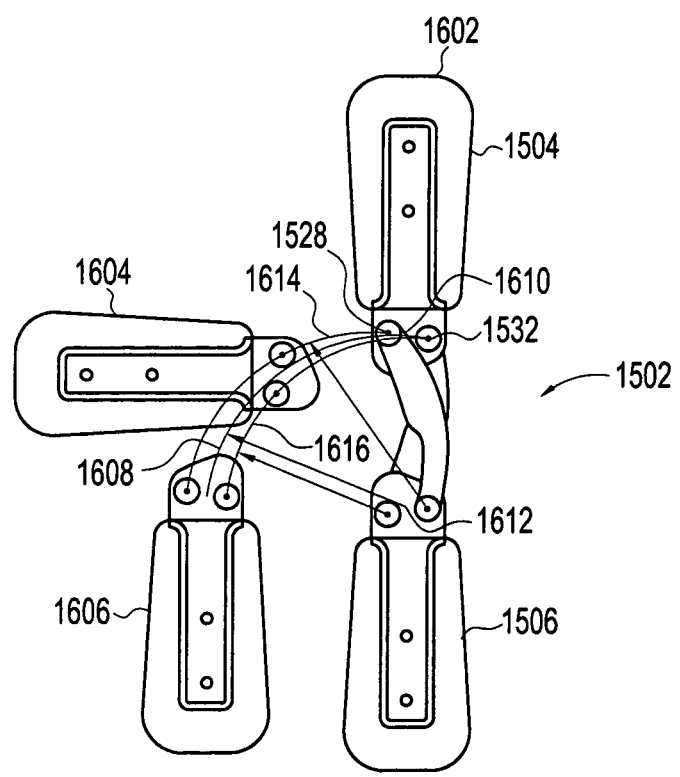
FIG. 16 shows an exemplary motion of a hinge assembly according to one embodiment of the invention.

The above-described motions of support portions 1504 and 1506 are further illustrated in FIG. 16. FIG. 16 shows cruciate hinge 1502 coupled between first, and second support portions. Support portion 1504 is shown in a first fully extended relationship 1602 with respect to support portions 1506, in a second partially lacks relationship 1604 and in a third fully flexed relationship 1606. It should be understood that the fully extended relationship 1602 and fully flexed relationship 1606 will not be achieved in some practical embodiments of the invention. Also illustrated is a substantially circular arc 1608 traversed by a pivot point 1610 during flexing of the cruciate hinge. Circular arc 1608 is centered at a further pivot point 1612. Also shown are corresponding arcs 1614 and 1616 defined by respective motions of the pivoting fasteners 1528, 1532.

Figure 17:
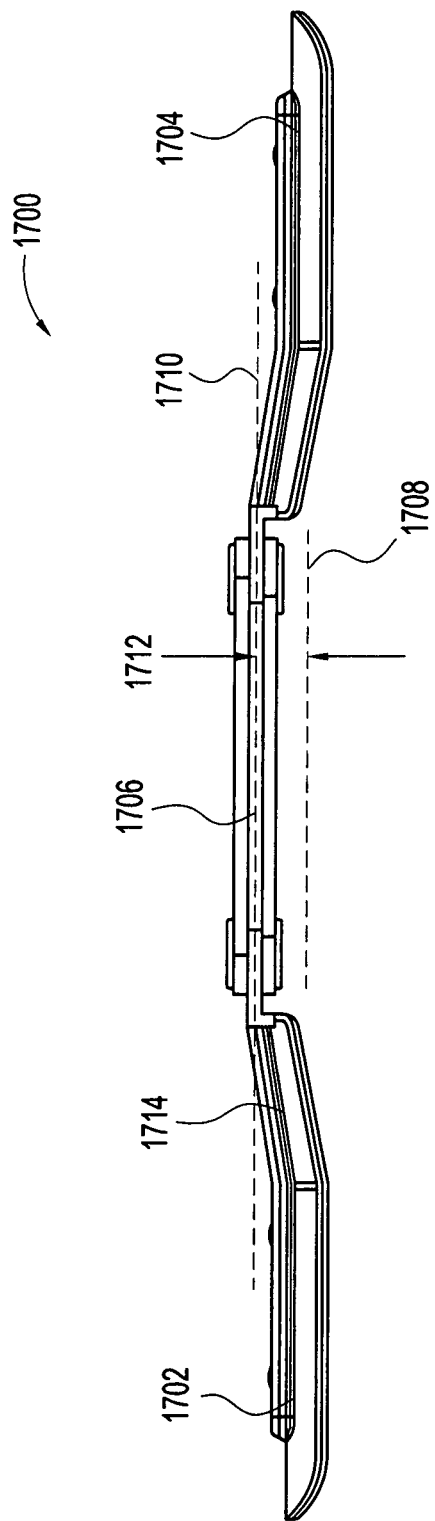
FIG. 17 shows, in side view, a hinge assembly according to one embodiment of the invention.

FIG. 17 shows a further aspect of the invention including a linkage device 1700 according to one embodiment of the invention. As illustrated, the linkage device 1700 includes first and second supporting portions (or paddles) 1702, 1704 and a hinge portion 1706. According to one embodiment of the invention, a plane of the paddle portion 1708 is offset from a plane of the hinge portion 1710 by a distance 1712. In various embodiments, this offset is achieved by a stepped or angled portion of the paddle of the linkage device, e.g., 1714.

Figure 18:
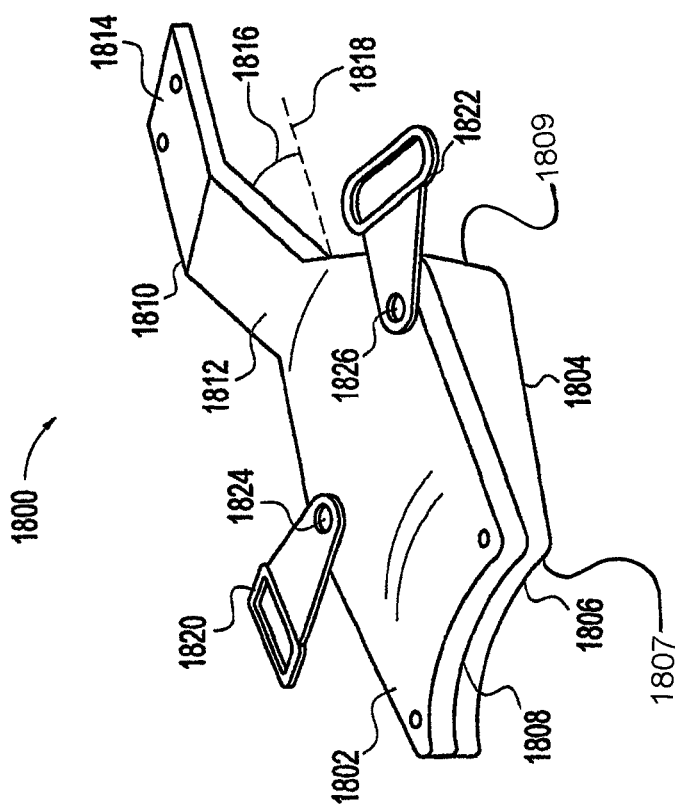
FIG. 18 shows, in perspective view, a paddle portion of a joint brace including a wedge-shaped cushion according to one embodiment of the invention.

FIG. 18 shows, in perspective view, a paddle portion of a joint brace 1800 according to one embodiment of the invention. In the illustrated embodiment, the paddle portion includes a substantially rigid supporting member 1802 and a wedge-shaped cushion portion 1804. The wedge-shaped cushion portion 1804 has a durometer adapted to allow deflection of a surface 1806 thereof so as to conform to a leg of a patient and apply a substantially uniform pressure to the leg. According to one embodiment of the invention, surface 1806 includes a substantially concave arcuate surface region. According to another embodiment of the invention, the substantially rigid supporting member 1802 includes a further substantially concave arcuate surface region 1808 adapted to support the wedge-shaped cushion portion 1804. As is evident upon inspection, surface region 1806 diverges from surface region 1808 between a first terminal end 1807 and a second terminal and 1809.

As illustrated, the substantially rigid supporting member 1802 also includes a mounting portion 1810 including an elevating member 1812 and a flange member 1814. According to the illustrated embodiment of the invention, the elevating member 1812 is disposed at acute angle 1816 with respect to a longitudinal axis 1818 of the concave surface region 1808. In other embodiments of the invention, angle 1816 is an obtuse angle, and in still other embodiments of the invention, angle 1816 is a right angle. As illustrated, elevating member 1812 serves to dispose flange portion 1814, and consequently a hinge device coupled to flange portion 1814 in an offset relationship with respect to surfaces 1806 and 1808.

In the illustrated embodiment, the substantially rigid supporting member 1802 is formed as an integral unit with elevating member 1812 and flange member 1814. According to various embodiments, this integrated arrangement is formed by injection molding or by thermal deformation of a thermoplastic blank. In other embodiments of the invention, the substantially rigid supporting member 1802 is formed by an assembly of components including one or more of the elevating member 1812 and a flange member 1814.

In certain embodiments the substantially rigid supporting member includes one or more of a thermoplastic, polymer material such as, for example, a polyethylene material, a polypropylene material, and ABS plastic material, or a thermoset polymer material such as, for example, phenol formaldehyde resin, epoxy resin, polyamide, and combinations thereof. In certain embodiments, a filler and/or reinforcing material is included within the polymer material such as, for sample, glass fiber, graphite fiber, nanotube fiber, metallic fiber, ceramic fiber and other fibrous and non-fibrous materials.

Also illustrated in FIG. 18 are a flange-mounted loop 1820 and a flange mounted buckle receptacle 1822. As illustrated, the flange mounted loop 1820 and flange mounted buckle receptacle 1822 are pivotally coupled to the substantially rigid supporting member 1802 by respective fastener devices 1824, 1826.

FIG. 19 shows, in perspective view, a portion of a joint brace 1900 according to another embodiment of the invention. As illustrated, the joint brace 1900 includes first 1902 and second 1904 paddle portions. Disposed between, and coupling together, the first and second paddle portions 1902, 1904 is a cruciate hinge device 1906. The cruciate hinge device 1906 includes first 1908 and second 1910 bearing members. The bearing members 1908, 1910 are pivotally coupled to the paddle portions 1902, 1904 at respective flange regions 1912, 1914 thereof. In the illustrated embodiment, this coupling is achieved by fasteners 1916, 1918, 1920, 1922 such as, for example rivets, screws or other fastener devices is known in the art. The fasteners are disposed, in the illustrated embodiment, within respective aligned through holes of the support members and flange portions. According to one embodiment of the invention, spacers 1924, 1926 are disposed around the fasteners, and include respective surface regions 1928, 1930.

The surface regions 1928, 1930 are adapted to contact corresponding surface regions of the bearing members 1908, 1910, thereby controlling a range of motion of the paddle portions 1902, 1904. According to an aspect of one embodiment of the invention, the hinge device 1906 is offset from a level of the paddle portions 1902, 1904 by an offset distance 1932.

According to the illustrated embodiment, the bearing members 1908, 1910 are shown to be of substantially equal length with respect to one another. In other embodiments of the invention, however, the bearing members 1908, 1910 have different lengths according to the requirements of a particular therapeutic application. In addition, peripheral edges of the bearing members may be straight or arcuate or angular according to requirements of a particular application.

FIG. 20a shows, in perspective view, a further portion of a joint brace according to one embodiment of the invention. As illustrated in FIG. 20a, bumper devices 2002, 2004 are adapted to be disposed about respective fasteners or spacers, such as those illustrated in FIG. 19. In certain embodiments of the invention, the bumper devices are formed of more or less resilient material such as, for example, any of the elastomers or polymers identified above. In certain embodiments, the bumper devices are formed as open toroidal devices including a central aperture for receiving a respective fastener or spacer. In other embodiments, the bumper devices are formed as closed cap-style devices including a cavity for receiving a respective fastener or spacer. According to certain embodiments of the invention, bumper devices of various sizes are to be used, and may be permanently or removably positioned about the fasteners and/or bumpers so as to provide an adjustable range of motion of the paddle devices 2006, 2008.

FIG. 20b shows an aspect of a further embodiment of the invention including a bumper 2010 comparable to that shown in FIG. 20a. Unlike the exemplary bumper 2002 of FIG. 20a, bumper 2010 includes an internal surface 2012 that is offset, i.e., not coaxial with external surface 2014. Consequently, by rotating bumper 2010 around a spacer on which it is disposed, different regions of surface 2014 can be presented to a bearing member 1908. Thus, in one orientation of the bumper 2010, a relatively narrow portion of the bumper 2016 is presented to the bearing member 1908, allowing for a relatively large range of motion of the joint brace. In another orientation of the bumper 2010, a relatively wide portion of the bumper 2018 is presented to the bearing member 1908, allowing for a relatively small range of motion of the joint brace.

FIG. 20c shows a further aspect of another embodiment of the invention including a further bumper 2020. Like bumper 2010, bumper 2020 is adapted to be disposed in a plurality of orientations and to present a corresponding plurality of spacing, including, a narrowest spacing 2022 and a widest spacing 2024 to the corresponding bearing member 1908 so as to adjust, correspondingly, a range of motion of the joint brace.

Figure 21:
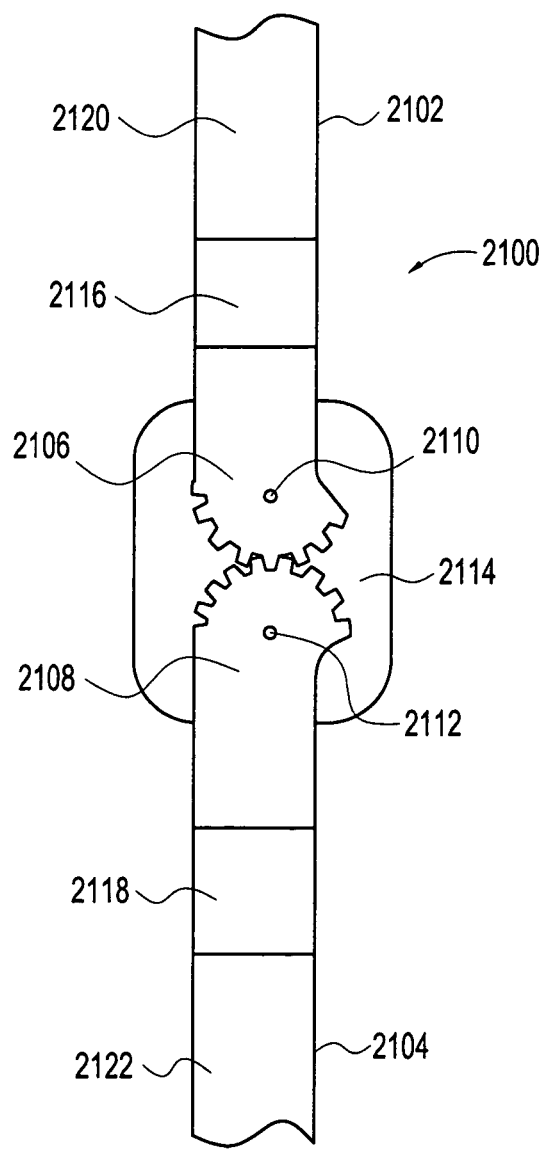
FIG. 21 shows a further hinge assembly adapted for use in a joint brace according to another embodiment of the invention.

FIG. 21 shows a further bi-axial hinge device 2100 according to another embodiment of the invention. According to the illustrated embodiment, the biaxial hinge device includes first 2102 and second 2104 supporting members having respective pinion portions 2106, 2108. The pinion portions 2106, 2108 are disposed to mesh respective teeth thereof, and to rotate about respective supporting axles 2110, 2112. A locator plate 2114 is provided to support the supporting axles 2110, 2112 in substantially parallel spaced relation with respect to one another. According to the illustrated embodiment, the supporting members 2102, 2104 have respective offset regions 2116, 2118 adapted to provide a displacement between a plane of the locator plate 2114 and respective supporting surface regions 2120, 2122 of the supporting members 2102, 2104. As in the embodiments described above, respective surfaces of the offset regions 2116, 2118 are, in various embodiments, disposed at an oblique angle, or at right angles, with respect to supporting surface regions 2120, 2122.

Figure 22:
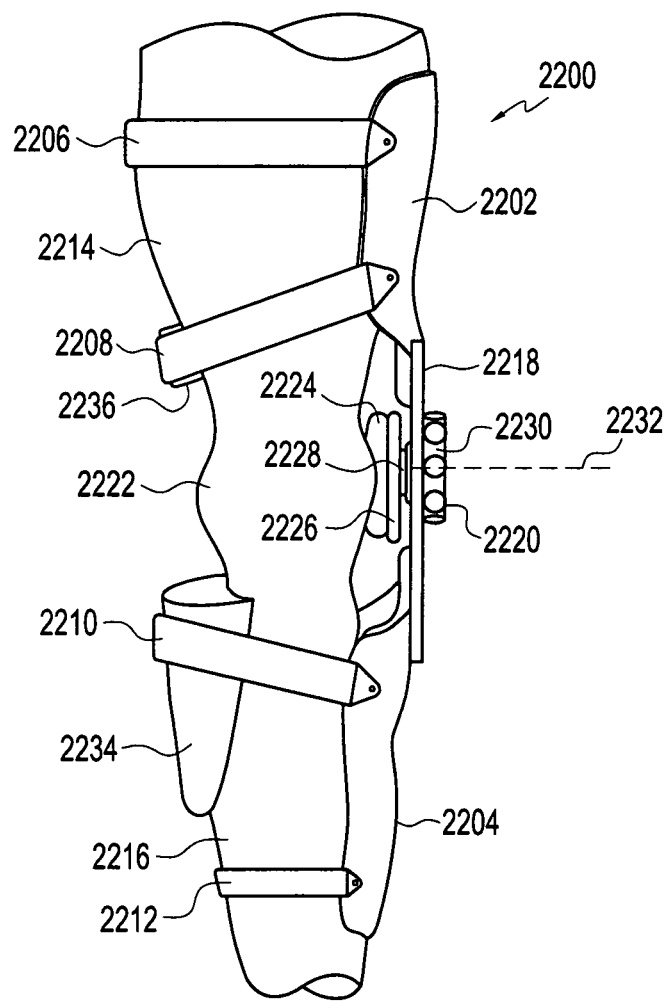
FIG. 22 shows, in perspective view, a joint brace according to yet another embodiment of the invention.

FIG. 22 shows a further embodiment of the invention including a joint brace 2200. The joint brace 2200 includes first 2202 and second 2204 paddle portions having respective surface regions adapted to be disposed adjacent to, for example, a leg of a patient. Location straps 2206, 2208, 2210, 2212 are provided to securely couple the first and second paddle portions 2202, 2204 adjacent to, for example, the thigh 2214 and the calf 2216 of the patient's leg. A hinge portion 2218 is disposed between, and couple two, the first and second paddle portions 2202, 2204, and adapted to provide a pivotal relationship between them. In the illustrated embodiment, a condyle compression device 2220 is coupled to the hinge device 2218. The condyle compression device is adapted to apply a force between the hinge portion 2218 and a knee 2222 of the patient's leg.

In one embodiment of the invention, as illustrated, the condyle compression device 2220 is an adjustable condyle compression device and includes a condyle pad 2224, a backplate 2226, a support member 2228 and an adjustment knob 2230. In one embodiment, the support member 2228 includes an external surface having a plurality of external threads. A corresponding internal surface of the adjustment knob 2230 includes an appropriate plurality of internal threads adapted to be coupled to the external threads of the support member 2228, such that a rotation of adjustment knob 2230 about a longitudinal axis 2232 results in a longitudinal motion of the support member 2228, and of the backplate 2226 and condyle pad 2224, along the longitudinal axis 2232. Accordingly, by an appropriate rotation of the knob 2230 a desired force can be applied to the knee 2222.

While the illustrated embodiment shows a threaded expansion device including support member to 2228 and knob 2230, the creative practitioner of ordinary skill in the art will appreciate that a wide variety of force-applying mechanisms may be substituted for the illustrated embodiment. Therefore, in various embodiments a hydraulic device, a pneumatic device, a mechanical device including, for example a scissors mechanism, or any other appropriate active or passive device may be employed.

In the illustrated embodiment, the locator straps 2206, 2208, 2210, 2212 are pivotally coupled to the paddle portions 2202, 2204. In other embodiments of the invention, slots provided in the paddle portions are adapted to receive the locator straps, or other fastening devices and methods, as known in the art, are employed to operatively coupled a straps to the paddle portions. In certain embodiments, the straps are substantially inelastic and provided with adjustment mechanisms to allow for firm placement around the subject leg. In a still further embodiment, the straps are substantially elastic and expandable or retractable according to a local circumference of the leg. In still a further embodiment of the invention, as shown, one or more pads, e.g., 2234 are provided between an internal surface of the locator straps, e.g., 2210. As illustrated by pad 2234, such pads may be relatively large and, in certain advantageous embodiment, are wedge-shaped. Also, in the case of exemplary pad 2234, it should be noted that the pad includes a concave surface adapted to be disposed adjacent to an external surface of the patient's leg.

In other embodiments, as illustrated by pad 2236, a pad may be relatively small and may be entirely disposed beneath a surface region of the corresponding locator strap, e.g., 2208. It should be appreciated that while various pads are shown in particular locations in various illustrated embodiments, any combination of size or location of pad is considered to be within the scope of the invention. In addition, it should be understood that in various embodiments, no pad is required, and that the location straps are disposed directly adjacent to a leg of the patient, and that in still further embodiments, a location straps incorporates a padded lining or other conformal surface.

In one advantageous embodiment, a joint brace is provided with both a removable condyle pad assembly adapted for installation on a hinge side of the brace, as shown for example in FIG. 22 (hinge side pad), and with a removable condyle pad adapted for installation opposite to a hinge side of the brace, as shown for example in FIG. 6 (opposite side pad). According to one exemplary method of the invention the joint brace is installed using one or the other of the hinge side pad and the opposite side pad. In this way, for example, a force such as force 218 of FIG. 2 can be applied to either the medial or lateral side of the affected joint, as required, while maintaining the hinge on a preferred site of the joint, such as the lateral side of the joint. According to one embodiment of the invention, a kit is provided including both a hinge side pad and an opposite side pad.

Figure 23B:
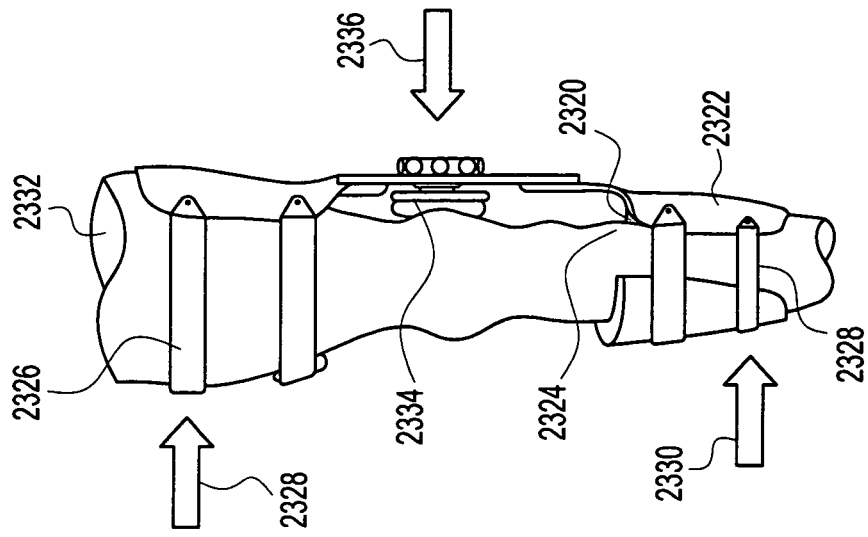
FIGS. 23a and 23b show further exemplary embodiments of the invention.
Figure 23A:
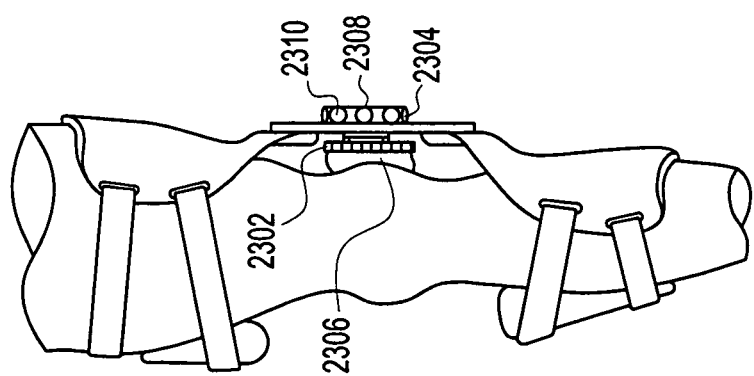

FIGS. 23a and 23b show further exemplary embodiments of the invention, including embodiment having location straps relatively distal with respect to the condyle, as compared with the embodiment of FIG. 22, and location straps adapted to be disposed in substantially parallel spaced relation with respect to one another. In a further aspect of one embodiment of the invention, support plate 2302 includes a circumferential surface having a plurality of grooves, knurls, or other features 2304 adapted to allow for comfortable gripping of the support plate 2302 during adjustment of the condyle pad 2306. In still a further aspect of the invention, according to one exemplary embodiment, an adjustment knob 2308 includes a circumferential surface having a plurality of grooves, knurls, or other features 2310 adapted to allow for comfortable gripping of the adjustment knob 2308 during adjustment of the condyle pad 2306.

In a further aspect of the invention, according to one embodiment, FIG. 23b shows a cushion or pad 2320 disposed between a supporting surface of an exemplary paddle 2322 and a corresponding supporting surface region of a patient's leg 2324. It will be appreciated by the creative practitioner of ordinary skill in the art that, in operation, location straps 2326 are adapted to provide respective first 2328 and second 2330 forces to the leg 2332 of the patient, relatively distal to the condyle, while condyle pad 2334 is adapted to apply a third force 2336 relatively proximate to the condyle.

Figure 24:
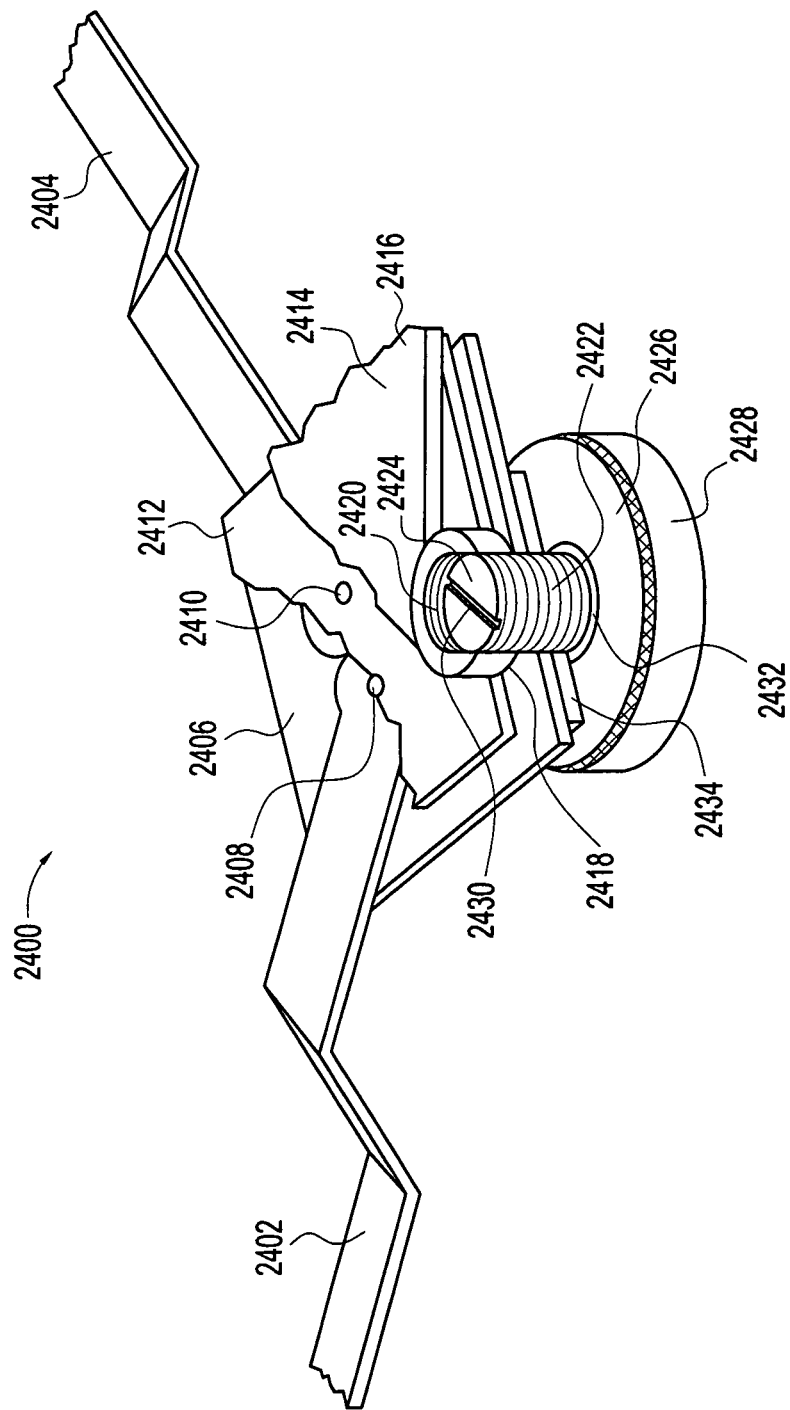
FIG. 24 shows, in perspective cutaway view, a hinge and condyle pad assembly according to still another embodiment of the invention.

FIG. 24 shows a further exemplary hinge device 2400 according to one embodiment of the invention. According to the illustrated embodiment, the hinge device 2400 includes first 2402 and second 2404 support members adapted to be pivotally coupled to a first baseplate member 2406 by first 2408 and second 2410 shaft members. A second baseplate member 2412 has a surface disposed in substantially parallel spaced relation to a corresponding surface of first baseplate 2406 so that the first and second support members 2402, 2404 are disposed therebetween. An adjusting knob 2414 includes a knob portion 2416 of relatively large radius and a hub portion 2418 of relatively small radius.

An internal surface 2420 of the hub portion 2418 defines a board therethrough, the internal surface 2420 bearing a plurality of internal threads thereupon. The internal threads are adapted to be threadingly coupled to a corresponding plurality of external threads on an external surface 2422 of a shaft 2424. The shaft 2424 is pivotally coupled at one end, according to one embodiment, to a backplate 2426 of the condyle pad device. The back plate 2426 is adapted to support a substantially elastic cushion portion 2428 on a surface thereof. According to the illustrated embodiment, an opposite end of the shaft includes a slot 2430 adapted to receive a portion of a tool such as, for example, a screwdriver therewithin.

According to one embodiment of the invention, the backplate 2426 includes a bearing device 2432 adapted to facilitate rotation of the backplate 2426 with respect to the shaft 2424 and consequently with respect to the baseplate members 2406 and 2412. In addition, according to the illustrated embodiment, a further bearing member such as, for example, a washer 2434 is provided between a surface of the backplate 2426 and a corresponding surface of the baseplate 2406, again to facilitate rotation of the backplate 2426 with respect to the shaft 2424 and the baseplate members 2406 and 2412. In various embodiments, one or more of the bearing device 2432 and the washer 2434 include a polymer material such as, for example, polyamide, polyaramid, Polytetrafluoroethylene (PTFE), or other substantially self lubricating material, as known in the art. In other embodiments, alternative bearing devices are provided including, for example, ball bearings, roller bearing, bronze oil bearings, and other bearings, including combinations thereof.

Figure 25:
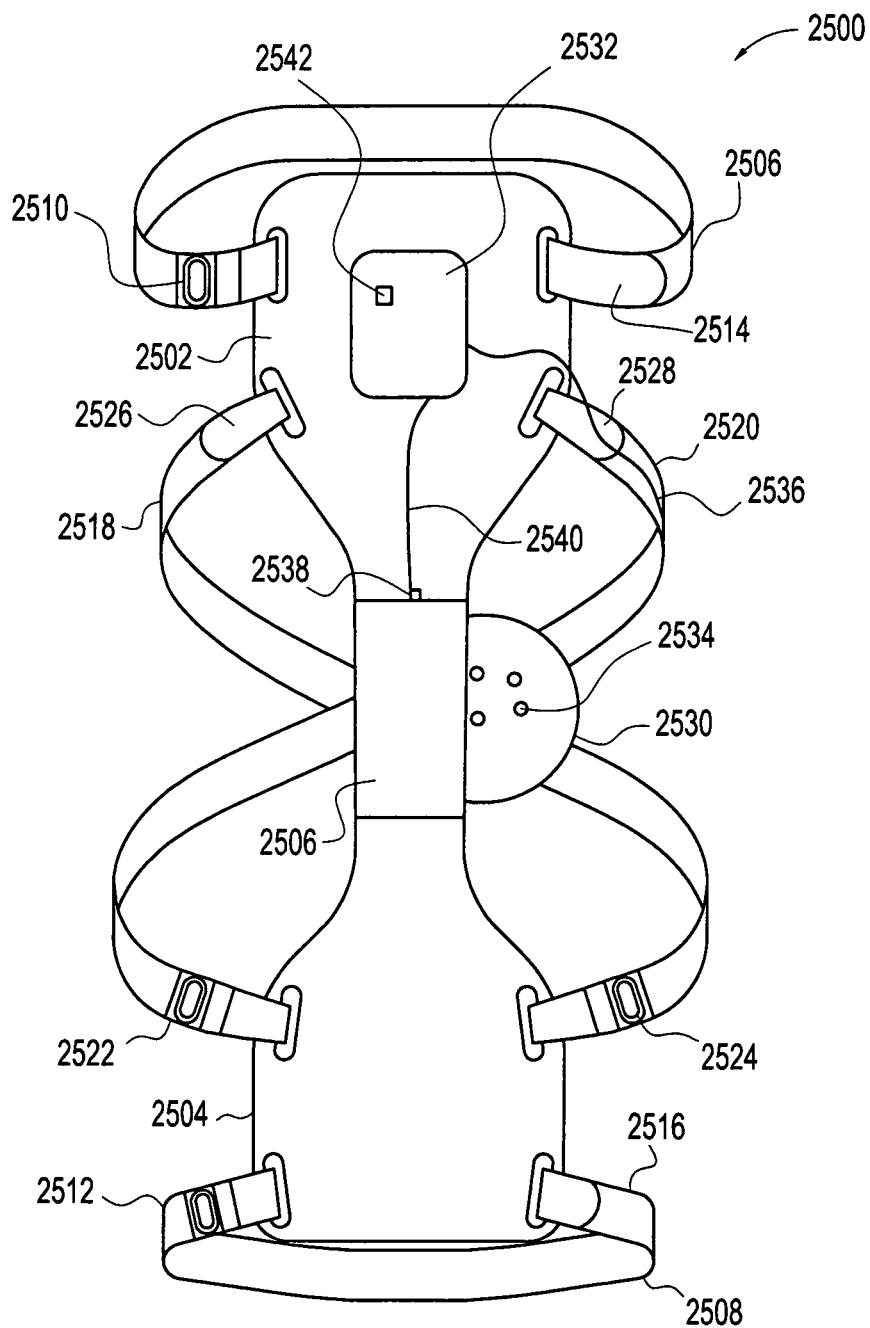
FIG. 25 shows a portion of a leg brace device including an electro-stimulation aspect according to another embodiment of the invention.

FIG. 25 shows a joint brace system 2500 including an electro-simulation portion according to a further embodiment of the invention. As illustrated, the joint includes first 2502 and second 2504 paddle portions and a joint portion 2506. First 2506 and second 2508 locator straps are coupled to the first and second metal portions 2502, 2504 respectively. In the illustrated embodiment, the locator straps 2506, 2508 include respective fastening clips 2510, 2512 and respective adjustment devices 2514, 2516. In the illustrated embodiment, the adjustment devices 2514, 2516 include hook and loop fastener devices, although other adjustment devices and arrangements as known in the art appropriate to various embodiments and applications of the invention.

The joint brace system 2500 also includes first 2518 and second 2520 tensioning straps with respective first 2522 and second 2524 fastening clips and respective first 2526 and second 2528 adjustment devices. The first and second tensioning straps 2518, 2520 are adapted to mutually support a condyle pad 2530.

According to the illustrated embodiment, the joint brace system 2500 also includes an electro-simulation device including, for example, a control portion 2532 and one or more electrode devices 2534 disposed, for example, at a patient-facing surface of the condyle pad 2530. In certain embodiments of the invention, the one or more electrode devices 2534 are coupled to the control portion 2532 by an electrical conductor 2536 such as an electrical wire or metallic strip, for example. In certain embodiments of the invention, the control portion 2532 is also coupled to a feedback sensor 2538 disposed, for example, at the hinge portion 2506 of the joint brace system. In the illustrated embodiment, the feedback sensor 2538 is signalingly coupled to the control portion 2532 by a signal conductor 2540 such as, for example, an electrical wire or optical fiber.

In certain embodiments, the joint brace system 2500 includes an operator control device such as, for example, a switch 2542 or other user interface device. In certain embodiments, the control portion 2532 includes a case portion which may be separately formed or integrally formed as a portion of the paddle 2502. In certain embodiments, the control portion 2532 also includes a power source such as, for example, an electrochemical cell, a capacitive electrical energy storage device, a mechanical energy storage device, a superconducting energy storage device, or an energy conversion device such as a thermoelectric device or a micro-turbine device, an electromagnetic generator or a capacitive generator. In certain embodiment of the invention, the power source is adapted to recover or receive energy from a motion or action of the hinge portion of the joint brace system 2500. In certain embodiments, the control portion 2532 also includes a regulation portion including, or example, a voltage regulation circuit or a current regulation circuit. In certain embodiments the control portion 2532 includes a processing device such as, for example, a microprocessor device or a microcontroller device. According to other embodiments of the invention, the sensor device 2538 include, for example, a mechanical switch device, a capacitive switch device, and accelerometer device, or other device adapted to detect a motion or action of the joint brace system 2500. Accordingly, in response to one or more of power and a sensor signal received at the controller device 2532, the controller device 2532 is adapted to provide an electrically stimulating voltage and/or current at the one or more electrode devices 2534, so as to provide a therapeutic or other benefit to a patient wearing the joint brace system 2500.

Figure 26:
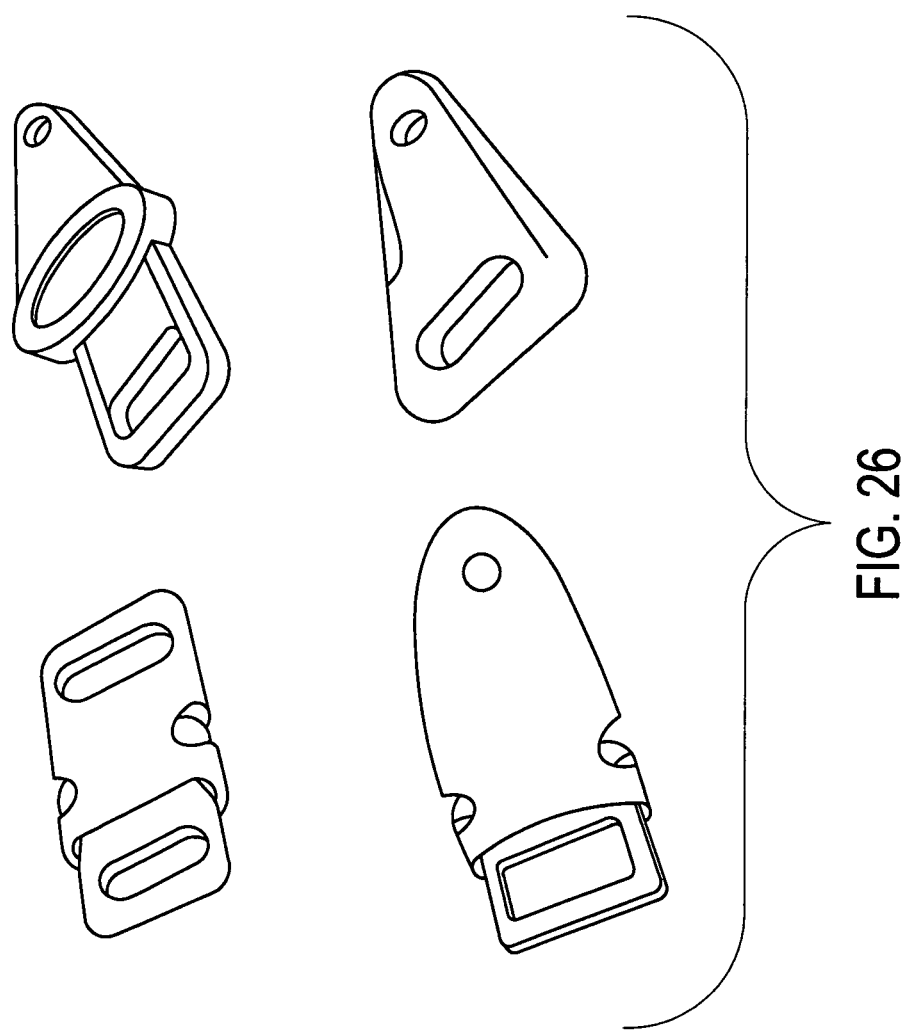
FIG. 26 shows various strap coupling devices adaptable for use in a joint brace according to certain embodiments of the invention.

FIG. 26 shows various exemplary strap coupling devices adaptable for use in particular embodiments of the invention. The strap coupling devices include quick release buckles having both vertical and lateral actuating clasp mechanisms. One of skill in the art will appreciate that the illustrated devices are exemplary of a wide variety of devices that would be readily applied by a creative practitioner of ordinary skill in the art according to particular applications, and in light of the various other novel features and characteristics of the invention as described above.

Figure 27:
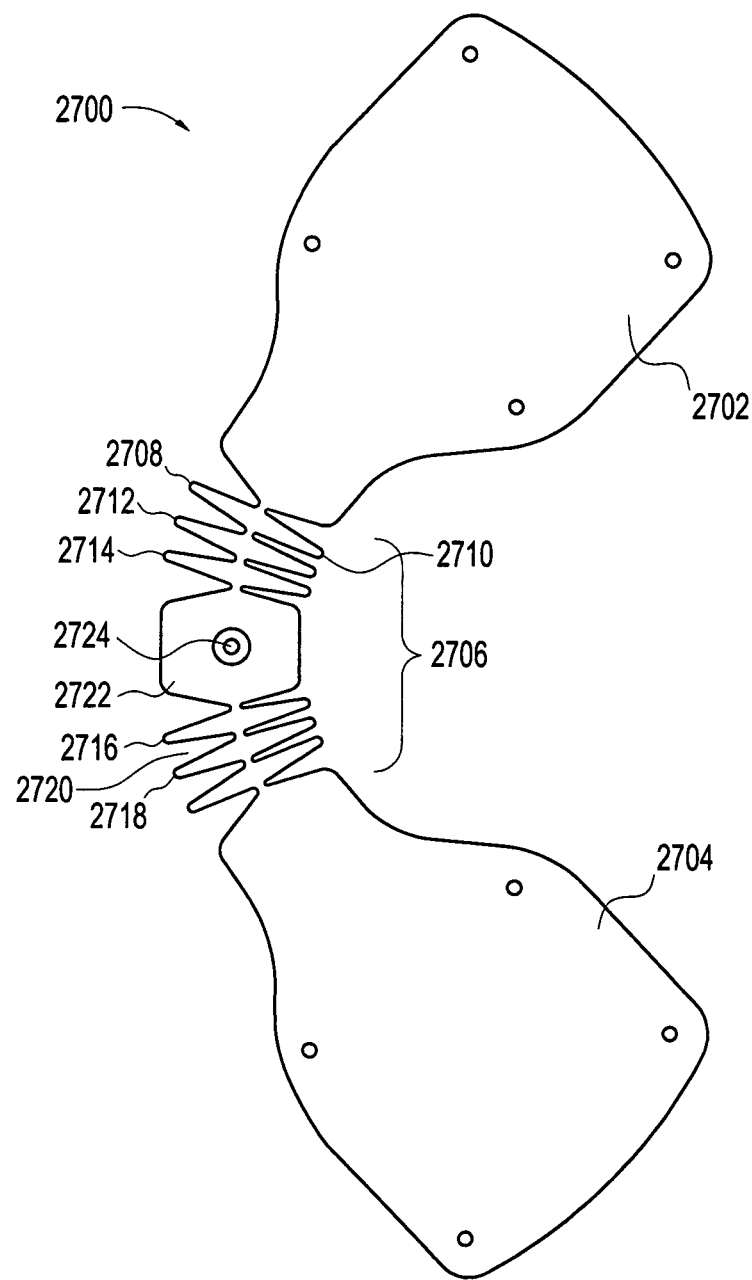
FIG. 27 shows a joint brace including a flexible hinge according to one embodiment of the invention.

FIG. 27 shows another embodiment of the invention including a joint brace having flexible hinge portion 2700. According to one embodiment of the invention, the joint brace 2700 includes first 2702 and second 2704 paddle portions and a hinge portion 2706 adapted to flex so as to allow a relative rotation of the first paddle portion 2702 with respect to the second paddle portion 2704. In one embodiment, the two paddles 2702, 2704 and the hinge are integrally formed as a single device. For example, in one embodiment, the paddle portions 2702, 2704 and hinge portion 2706 are molded together in a single injection molding process. In other embodiments the joint brace is formed as an assembly of components including a flexible hinge portion.

In the illustrated embodiment, joint brace 2700 includes a plurality of vane portions e.g., 2708, 2710, 2712 disposed locally perpendicular to a central member portion 2714. Respective surfaces of the vanes, e.g., 2716, 2718 are disposed to define a gap or slot 2720 therebetween. Accordingly, in operation, the central member portion 2714 is adapted to flex with a corresponding opening or closing of the slots e.g., 2720.

According to one embodiment of the invention, a portion of the hinge 2722 includes a through-hole 2724 disposed generally coplanar to the un-flexed central member portion 2714. Thus, in one embodiment, the through-hole is adapted to receive a shaft therethrough for supporting, for example, a condyle pad assembly. In one example embodiment, the condyle pad assembly is generally similar to condyle pad assembly 2400 of FIG. 24. According to one embodiment, a threaded insert is disposed within the through-hole to provide a robust engagement between, for example a threaded shaft of a condyle pad assembly and an internally threaded surface of the threaded insert.

Figure 28:
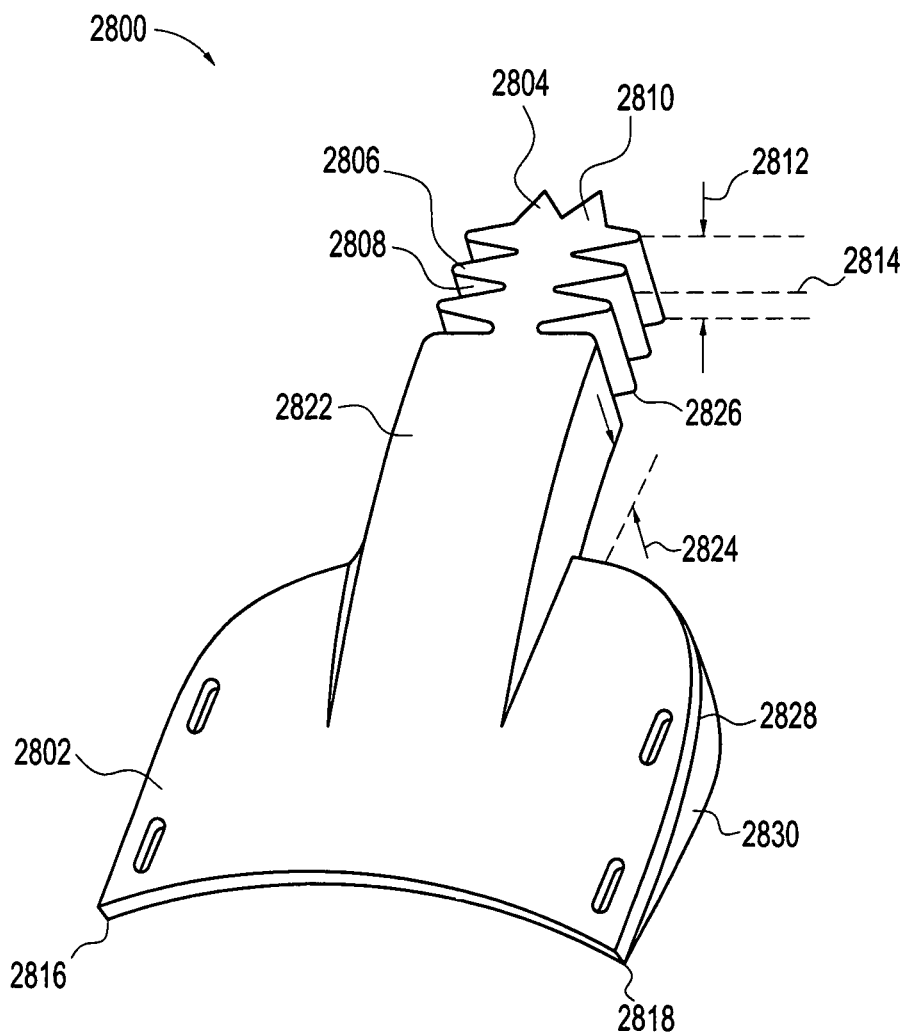
FIG. 28 shows a portion of a joint brace including a flexible hinge according to a further embodiment of the invention.

FIG. 28 shows, in perspective view, a portion of a further joint brace 2800 according to one embodiment of the invention. In one aspect, the illustrated embodiment includes a paddle portion 2802 and hinge portion 2804. The hinge portion 2804 includes a plurality of vanes, e.g., 2806 disposed adjacent to a plurality of slots 2808. A central member portion or region 2810 is adapted to flex with a corresponding opening and closing of slots on opposite sides of the central portion 2810. A thickness 2812 of the hinge portion 2804 serves to substantially prevent flexing of the hinge portion about an axis 2814 so as to maintain paddle 2802, and a counterpart paddle (not shown) in a substantially constant mutual relationship to a plane defined by paddle corners 2816, 2818, and the corresponding corners of the opposing paddle (not shown).

As shown, the hinge portion 2804 is coupled to the paddle portion 2802 by a coupling portion 2822. In one embodiment, the coupling portion is shaped to provide an offset distance 2824 between a patient-side surface region 2826 of the hinge portion 2804 and a patient-side surface region 2828 of the paddle 2802. In one embodiment, this offset is adapted to provide a space allowing the placement of a condyle pad portion between the patient-side surface region 2826 of the hinge portion 2804 and the patient's joint.

In still other embodiments of the invention, a flexible hinge joint brace is produced by coupling a plurality of layers of material such as, for example, a flexible polymer material, to one another. Thus, in one embodiment, a plurality of layers includes a first layer including a paddle portion, and further layers including respective vanes and slots. In one embodiment of the invention, a flexible hinge is formed by coupling first and second serpentine members adjacent to one another between respective supporting portions of first and second paddle portions.

According to one embodiment of the invention, paddle portion 2802 includes a cushion portion 2830. In various embodiments, cushion portion 2830 is formed in place as an integral portion of paddle portion 2802. In other embodiments, cushion portion 2830 is a discrete device adapted to be coupled to paddle portion 2802.

In various embodiments a flexible-hinge joint brace according to the invention is includes a polymer material such as, for example, polyethylene, ultrahigh molecular weight polyethylene, polypropylene, polybutylene, ABS plastic, urethane, neoprene and other natural and synthetic polymers, and combinations thereof. In still other embodiments, the joint brace includes one or more metallic materials such as, for example, stainless steel and spring steel. In certain embodiment, the joint brace is formed by molding (as in, e.g., injection molding), by vacuum molding, by machining (for example to form slots 2808 as shown in FIG. 28) by stamping, by electrochemical milling, by sputtering, by chemical vapor deposition, or by other manufacturing methods as known or as become known to the creative practitioner of ordinary skill in the art.

Figure 29:
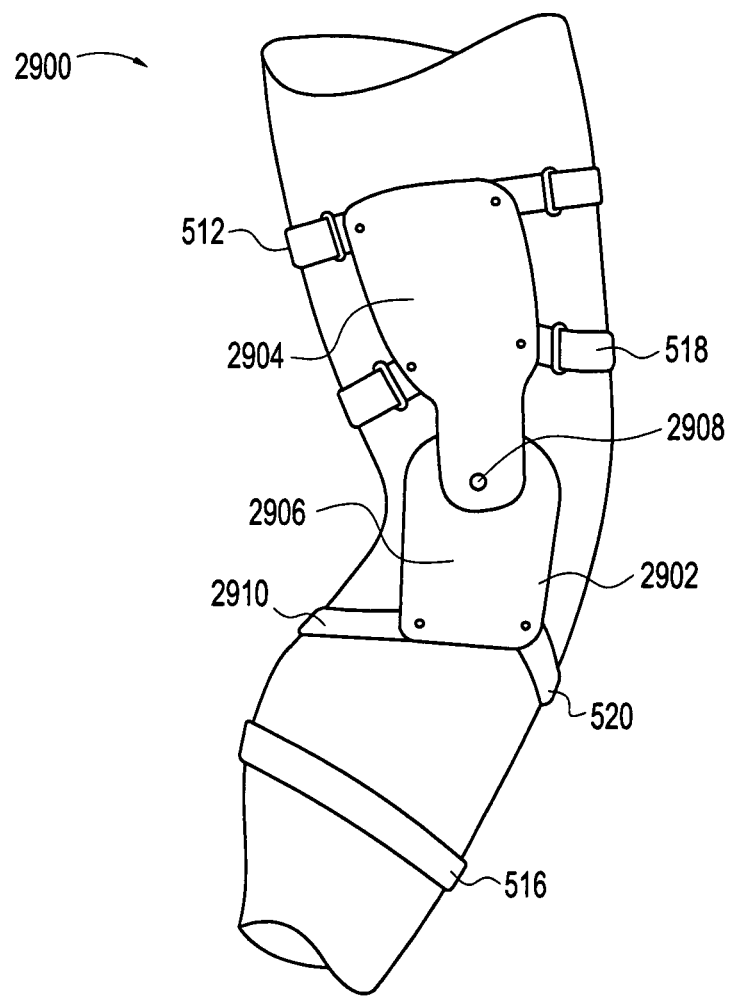
FIG. 29 shows a portion of a joint brace including a hybrid condyle pad assembly according to a further embodiment of the invention.

FIG. 29 shows a joint brace 2900 according to a further embodiment of the invention. As shown, brace 2900 includes a condyle pad assembly 2902 having a first paddle portion 2904 and a second backplate portion 2906. Referring again to FIG. 5, discussed above, the backplate portion 2906 is disposed on the opposite side of a knee joint from a hinge portion 502. Accordingly, strap 512 is disposed between paddle portion 504 and paddle portion 2904. Similarly, strap 518 is disposed between paddle portion 504 and paddle portion 2904. In the illustrated embodiment, backplate portion 2906 is pivotally coupled to paddle portion 2904 at a joining device such as an axle 2908. In various embodiments, the axle 2908 includes a rivet device, a nut and bolt device, an integral stud projecting from one or the other of the paddle portion 2904 or the backplate portion 2906 or another fastener device, such as would be known in the art.

In the illustrated embodiment, straps 520 and 2910 are respectively disposed between paddle 506 and backplate 2906. A further strap 516 is also disposed between paddle 506 and backplate 2906, as shown. Strap 516 is arranged to hold paddle 506 firmly against a calf of the patient, as shown. According to one embodiment of the invention, both strap 516 and strap 520 are substantially inelastic along longitudinal axes thereof. In a further embodiment, both are adjustable to allow for proper positioning of the backplate 2906, and of a condyle pad coupled to the backplate (not shown) with respect to the patient's joint. In a further embodiment of the invention, one or more of straps 512 and 518 are substantially elastic along longitudinal axes thereof.

Figure 30:
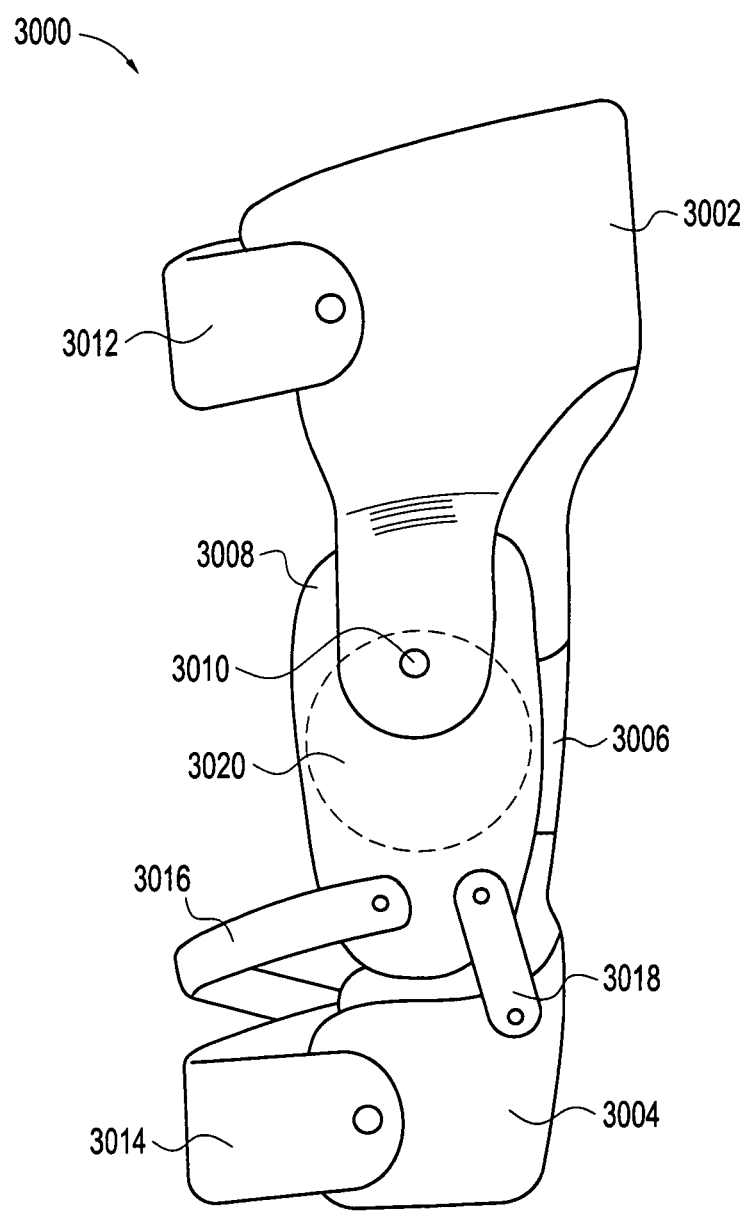
FIG. 30 shows a further joint brace.

FIG. 30 shows a further brace device 3000. In the illustrated embodiment, brace device 3000 includes first 3002 and second 3004 demi-cuff portions with a hinge portion 3006 disposed therebetween. As shown, condyle pad assembly 3008 is disposed in spaced relation with respect to the hinge portion 3006. The condyle pad assembly 3008 is pivotally coupled to demi-cuff 3002 at an axle 3010. In various embodiments, the axle 3010 includes a rivet device, a nut and bolt device, an integral stud projecting from one or the other of the demi-cuff portion 3002 or the condyle pad assembly 3008, or another fastener device, such as would be known in the art.

As illustrated, straps 3012 and 3014 are adapted to couple demi-cuffs 3002 and 3004 to the thigh and calf of the patient respectively. Straps 3012 and 3014 are substantially inelastic along respective longitudinal axes thereof. As illustrated, strap 3016 is also substantially inelastic along a longitudinal axis thereof, whereas strap 3018 is substantially elastic along a longitudinal axis thereof, and adapted to permit a self-positioning action of the condyle pad assembly, including a condyle pad 3020 with respect to a knee joint of the patient.

Figure 31:
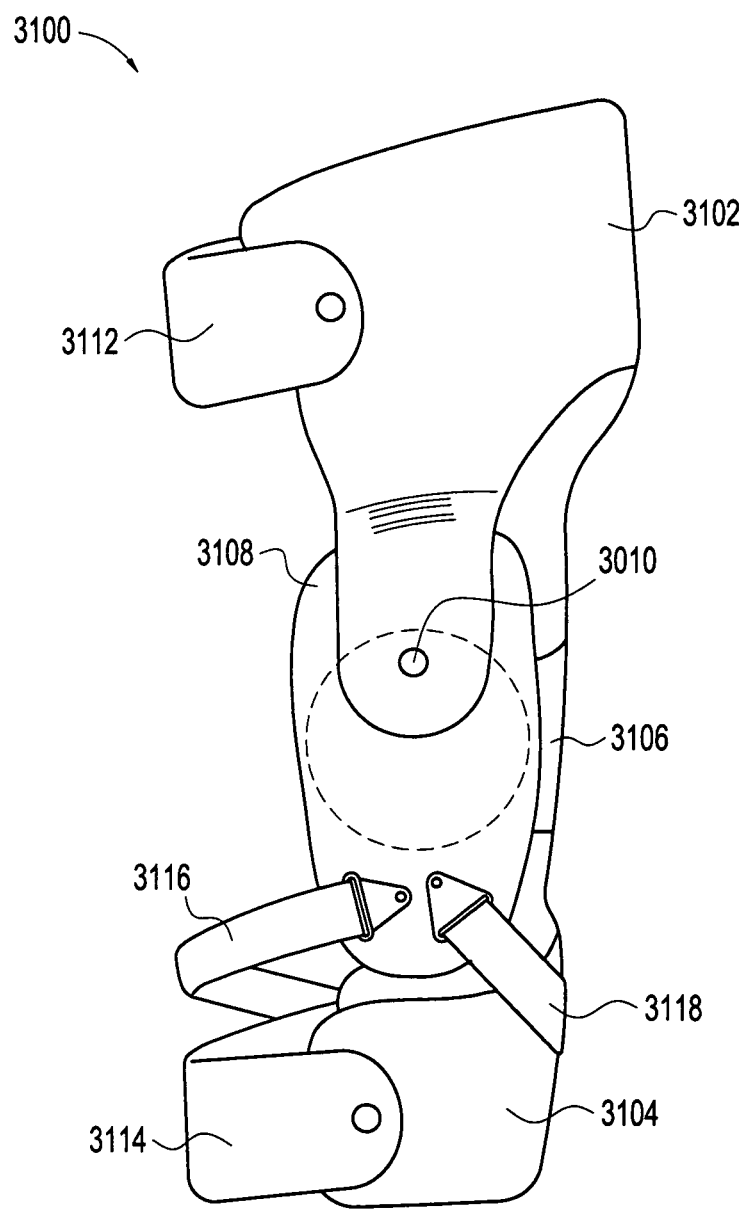
FIG. 31 shows a portion of a further joint brace according to another embodiment of the invention.
Figure 35A:
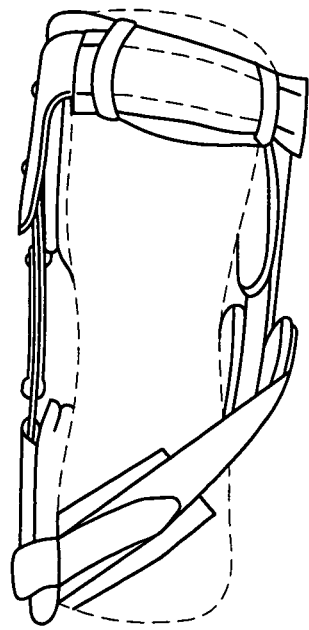
FIGS. 35a-35d show, in various views, a joint brace illustrating aspects of the invention.
Figure 35B:
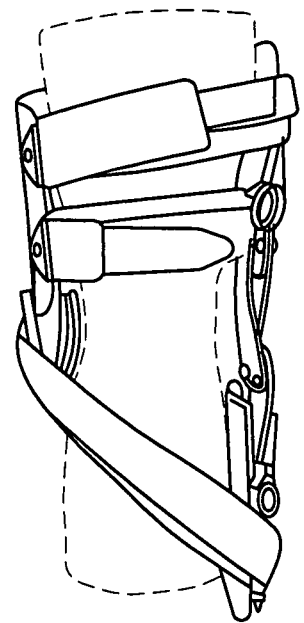
Figure 35C:
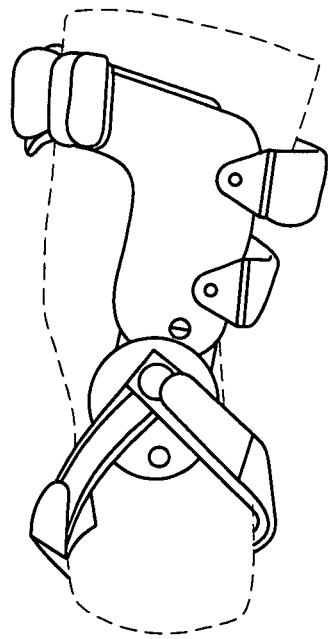
Figure 35D:
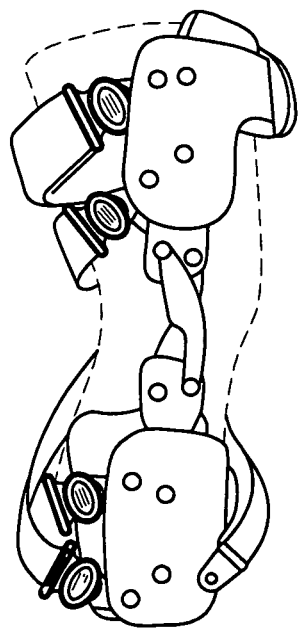

FIG. 31 shows a joint brace 3100 according to a further embodiment of the invention. Like joint brace 3000, joint brace 3100 includes first 3102 and second 3104 demi-cuffs, a hinge portion 3106, a condyle pad assembly 3108 pivotally mounted to demi-cuff 3102 at an axle 3110. According to the illustrated embodiment, demi-cuffs 3102 and 3104 include a substantially rigid material such as, for example, a synthetic polymer material or a metallic material. One of skill in the art will appreciate that other materials such as, for example, natural polymer materials and leather may also be employed in the demi-cuffs.

In the illustrated embodiment, straps 3112 and 3114 include straps having a substantially inelastic characteristic along respective longitudinal axes thereof. In like fashion, according to one embodiment, straps 3116 and 3118 are substantially inelastic along respective longitudinal axes thereof. Accordingly, by adjusting a tension of strap 3116 and by adjusting a tension of strap 3118, a force can be applied through condyle pad assembly 3108 to the knee joint of a patient so as to cantilever the knee joint of the patient. This application of forces can serve to unload a medial or lateral portion of the patient's articular cartilage, depending on an application of the brace.

A brace, similar to brace 3000 of FIG. 30, and including an elastic strap 3018, is known in the treatment of a human knee joint having a damaged anterior cruciate ligament or a damaged medial cruciate ligament. Surprisingly, however, it has been found that by providing a substantially inelastic strap disposed as shown 3118 in the brace 3100 of FIG. 31 a brace is operative to cantilever the joint and thus provide an efficacious treatment for an osteoarthritis condition. The illustrated novel disposition of first and second substantially inelastic straps 3116, 3118 in a substantially helical arrangement, produces forces that are new and different in direction and magnitude. Consequently, this modification makes the brace unexpectedly efficacious in the treatment of osteoarthritis. That such treatment value is unexpected is supported by the fact that long use of braces in the treatment of cruciate ligament damage by creative practitioners of skill in the art has nevertheless failed to expose the novel and beneficial advantages of the brace of the present invention.

FIG. 32a shows a joint brace 4900 and illustrates further embodiments and aspects of the invention. According to one aspect of the invention, the brace 4900 includes an upper location cuff portion 4902 and a lower paddle portion 4904. A hinge portion 4906 is disposed between, and coupled to, the upper location cuff portion 4902 and the lower panel portion 4904 at respective ends thereof.

In the illustrated embodiment, the hinge portion 4906 includes four rotationally interengaging devices 4908, 4910, 4912 and 4914. According to certain embodiments of the invention the interengaging devices 4908, 4910, 4912 and 4914 are implemented as interengaging toothed pinion gears. In light of the present disclosure, however, the creative practitioner of skill in the art will appreciate that alternative interengaging devices, such as, for example frictionally engaging devices will be employed advantageously in corresponding embodiments of the invention.

In the illustrated embodiment, device 4908 is adapted to be substantially rotationally fixed with respect to a supporting member 4916. In like fashion, device 4914 is adapted to be substantially rotationally fixed with respect to supporting member 4918. Devices 4910 and 4912 are disposed and arranged to engage with devices 4908 and 4914 respectively, and to couple a rotational displacement between supporting members 4916 and 4918.

FIG. 32*b* shows a hinge portion 4930 according to aspects of the invention in additional detail. As shown, a body member 4932 is disposed between supporting members 4934 and 4936. The body member 4932 is adapted to be mutually coupled to axle members 4938, 4940, 4942 and 4944. The axle members are disposed to support respective interengaging devices, here pinion gears 4946 and 4948, as well as supporting members 4934 and 4936.

It should be noted that in the illustrated embodiment, appropriate ends of the supporting members 4934 and 4936 include respective gear tooth formations adapted to engage pinion gears 4946 and 4948 respectively. Other arrangements are certainly possible, however, and fall within the scope of the present disclosure. Thus, whereas supporting member 4934 includes integral gear tooth portions, an alternative arrangement includes an assembly having a pinion gear coupled to a supporting member. As discussed above, in certain embodiments of the invention, supporting members 4934 and 4936 include respective angled regions 4935 and 4937.

One of skill in the art will appreciate that an even number of devices is advantageously employed in a hinge according to the invention. Thus, while four rotating devices are shown in the illustrated embodiment, other devices will be used where the requirements of a particular application suggest it. It will also be appreciated, that while for clarity a presentation, bearing or bushing devices are not expressly shown in the figures, it is understood that the use of such devices such as, for example, ball bearings, roller bearings, needle bearings, bronze bushings (including oil impregnated bronze bushings), polymer bushings (including nylon bushings, UHMWPE bushings, graphite and graphite impregnated bushings, nanotube and Buckminster fullerene impregnated bushings), and any other bearing and/or bushing appropriate a particular application, is intended to be included in the present disclosure. Also of use in various embodiments of the invention are pinion gears and bearing members including materials identified above and other appropriate metallic materials, polymer materials and combinations thereof.

FIGS. 33*a*-33*d* shows a brace similar to brace 4900 of FIG. 32*a*. It should be noted that, while a right-handed device is illustrated, the ordinarily creative practitioner will readily create a left-handed device by applying well-known principles of symmetry. Brace 4900 of FIG. 33*a* shows first, second, third and fourth rotationally interengaging devices 4908, 4910, 4912 and 4914. Respective axle members 4938, 4940, 4942 and 4944 are also shown; illustrated here as riveted members. In addition, an exemplary spacer 4950 is illustrated.

The practitioner of skill in the art will appreciate that condyle pad 4952, disposed in spaced relation to hinge portion 4906, is adapted to operate as described above. In addition, it will be understood that the presently disclosed arrangement is adapted to allow a hinge portion 4906 to be formed with a desirable spacing between axle 4938 and axle 4944 while maintaining a substantially fixed rotational relationship between supporting members 4916 and 4918.

In reviewing FIGS. 33*a*-33*d*, the practitioner of skill in the art will observe that the disclosed invention provides desirable support to a subject joint while being advantageously small and lightweight. In particular, it should be noted that the support cuff and paddle portions are adapted to support re-positionable cushion members using, for example, hook and loop fasteners. One desirable location for such a fastener is illustrated in FIG. 32*a*, and identified with reference number 4903.

FIG. 34*a* shows a further embodiment of the invention including joint brace 5000 having a support-cuff and paddle arrangement similar to that shown in FIGS. 32*a* and 33*a*-33*d*. Brace 5000, however, includes a cruciate hinge portion 5002 similar to that described above. In addition, in certain embodiments, an adjustable condyle pad 5004 is provided.

FIG. 34*b* shows one adjustable condyle pad 5004 adapted to be adjusted by inflation and/or deflation under the control of a medical professional and/or a user of the brace. The condyle pad 5004 includes a substantially flexible portion 5006 having a cavity disposed therewithin. A valve portion 5008 is adapted to receive a probe portion 5010 of an inflation device, such as the illustrated bulb pump 5012. Accordingly, an atmospheric region within the cavity can be pressurized or depressurized to a desirable level. Consequently, a desirable and adjustable overall durometer, or rigidity, of the condyle pad can be achieved.

FIGS. 35*a*-35*d* show a brace 5000 like that of FIG. 34*a* arranged as typically used. In light of these illustrations, and of the disclosure provided above, one of skill in the art will readily understand the application and adjustment of the inventive device.

While the exemplary embodiments described above have been chosen primarily from the field of human medicine, one of skill in the art will appreciate that the principles of the invention are equally well applied, and that the benefits of the present invention are equally well realized in a wide variety of other fields including, for example, veterinary medicine. Further, while the invention has been described in detail in connection with the presently preferred embodiments, it should be readily understood that the invention is not limited to such disclosed embodiments. Rather, the invention can be modified to incorporate any number of variations, alterations, substitutions, or equivalent arrangements not heretofore described, but which are commensurate with the spirit and scope of the invention. Accordingly, the invention is not to be seen as limited by the foregoing description, but is only limited by the scope of the claims appended hereto, and those later provided.

The invention claimed is:

1. A method of using a wedge for an orthotic brace comprising:

disposing a hinge device adjacent a limb of a patient, said hinge device including a first longitudinal member and a second longitudinal member mutually pivotally coupled to one another at respective proximal ends by a hinge feature, said first and second longitudinal members having respective first and second longitudinal axes, said first longitudinal axes disposed generally coplanar to a third longitudinal axis of a first bone of said limb, said second longitudinal axis disposed generally coplanar to a fourth longitudinal axes of a second bone of said limb, said first and second bones mutually pivotally coupled at a joint of said limb such that said joint and said hinge feature are generally aligned to rotate about a mutual axis of rotation, said first longitudinal axis arranged to approach said third longitudinal axis in a direction along said first longitudinal member away from said hinge feature and said second longitudinal axis arranged to approach said fourth longitudinal axis in a direction along said second longitudinal member away from said hinge feature;

disposing said wedge between an inner surface of said first member and an outer surface of said limb, said wedge arranged to have a relatively wide end proximal to said hinge feature and a relatively narrow end distal to said hinge feature, said wedge diverging monotonically from said relatively narrow end to said relatively wide end; and placing said wedge in compression by coupling said hinge device to said limb.

2. A method of using a wedge for an orthotic brace as defined in claim 1 wherein said placing said wedge in compression by coupling said hinge device to said limb comprises coupling a strap device circumferentially about a portion of said limb.

3. A method of using a wedge for an orthotic brace as defined in claim 2 wherein a longitudinal axis of said strap defines a plane, said third longitudinal axes intersecting said plane and substantially normal to said plane.

4. A method of using a wedge for an orthotic brace as defined in claim 2 wherein a longitudinal axis of said strap defines a plane, said third longitudinal axes intersecting said plane at an oblique angle such that said plane approaches said joint along a line from said first longitudinal axis to said third longitudinal axis.

5. A method of using a wedge for an orthotic brace as defined in claim 1 wherein said wedge includes a body portion, said body portion having first and second surfaces, said first and second surfaces diverging over a range from said relatively narrow end of said wedge to said relatively wide end of said wedge, said wedge being adapted to be disposed between a cuff portion of said orthotic brace and an outer surface of said limb.

6. A wedge as defined in claim 5 wherein said diverging of said first and second surfaces comprises a substantially monotonic divergence.

7. A wedge as defined in claim 5 wherein said body includes a substantially elastic material.

8. A wedge as defined in claim 7 wherein said substantially elastic material includes an open cell foam material.

9. A wedge as defined in claim 7 wherein said substantially elastic material comprises a closed cell foam material.

10. A wedge as defined in claim 7 wherein said substantially elastic material comprises a natural polymer material.

11. A wedge as defined in claim 7 wherein said substantially elastic material comprises a natural rubber.

12. A wedge as defined in claim 7 wherein said substantially elastic material comprises a synthetic polymer material.

13. A wedge as defined in claim 7 wherein said substantially elastic material comprises a neoprene material.

14. A wedge as defined in claim 7 wherein said substantially elastic material comprises a polyurethane material.

15. A wedge as defined in claim 5 wherein said orthotic brace further comprises:
a further cuff portion;
said hinge feature being disposed between said cuff portion and said further cuff portion; and
wherein said orthotic brace is adapted to place a joint of said patient's limb in a cantilevered condition.

16. A wedge as defined in claim 15 wherein said cantilevered condition comprises a relieved load at a portion of said joint.

17. A wedge as defined in claim 16 wherein said joint comprises a human knee joint.

18. A wedge as defined in claim 15 wherein said hinge device comprises a cruciate hinge device.

19. A wedge as defined in claim 15 wherein said further cuff portion is adapted to support a further wedge.

20. A wedge as defined in claim 15 wherein said orthotic brace further comprises a condyle pad.

21. A wedge as defined in claim 20 wherein said condyle pad comprises an adjustable condyle pad.

22. A wedge as defined in claim 21 wherein said adjustable condyle pad comprises a pneumatic adjustment device.

\* \* \* \* \*